US012700510B2

(12) United States Patent
Zhang et al.

(10) Patent No.: US 12,700,510 B2
(45) Date of Patent: Aug. 4, 2026

(54) SYSTEM AND METHOD FOR IMPROVING PATIENT TREATMENT

(71) Applicant: UNIVERSITY OF MARYLAND MEDICAL SYSTEM CORPORATION, Linthicum Heights, MD (US)

(72) Inventors: Hao Howard Zhang, Potomac, MD (US); William Porter Bame, Hampstead, MD (US); Enhao Liu, Hanover, MD (US); Colleen Michelle Ennett, Eldersburg, MD (US); Warren Dean D'Souza, Towson, MD (US)

(73) Assignee: UNIVERSITY OF MARYLAND MEDICAL SYSTEM, Linthicum Heights, MD (US)

( * ) Notice: Subject to any disclaimer, the term of this patent is extended or adjusted under 35 U.S.C. 154(b) by 87 days.

(21) Appl. No.: 18/625,657

(22) Filed: Apr. 3, 2024

(65) Prior Publication Data

US 2025/0316394 A1       Oct. 9, 2025

(51) Int. Cl.
*G16H 50/70*       (2018.01)
*G16H 10/60*       (2018.01)

(52) U.S. Cl.
CPC ............. *G16H 50/70* (2018.01); *G16H 10/60* (2018.01)

(58) Field of Classification Search
None
See application file for complete search history.

(56) References Cited

U.S. PATENT DOCUMENTS 10,558,627 B2      2/2020   Cassidy et al.
10,679,746 B1      6/2020   Fletcher et al.
(Continued)

OTHER PUBLICATIONS

Barnes S, Hamrock E, Toerper M, Siddiqui S, Levin S. Real-time prediction of inpatient length of stay for discharge prioritization. J Am Med Inform Assoc. Apr. 2016;23(e1):e2-e10. doi: 10.1093/jamia/ocv106. Epub Aug. 7, 2015. PMID: 26253131; PMCID: PMC4954620. (Year: 2015).*

(Continued)

*Primary Examiner* — Mamon Obeid
*Assistant Examiner* — Ashley Elizabeth Evans
(74) *Attorney, Agent, or Firm* — Lando & Anastasi, LLP

(57) ABSTRACT

Examples of the disclosure include a method of operating a patient-discharge-optimization system to improve medical outcomes, the method comprising: accessing, from memory and/or storage, historical patient flow information including a plurality of timestamped events for each of a plurality of patients; converting, by the discharge-optimization system, the historical patient flow information into standardized flow information having a standardized format defined by a plurality of standardized parameters; generating, by the discharge-optimization system, a plurality of models, each model indicating an effect of modifying at least one parameter of the standardized parameters for each of the patients; deriving, by the discharge-optimization system and based on the models, an optimal discharge histogram for one or more days; forecasting, based on the historical patient flow information, an anticipated future number of discharges for the day(s); deriving an optimal patient discharge timetable for the day(s); and providing the optimal patient discharge timetable to users.

20 Claims, 14 Drawing Sheets

(56)        References Cited

U.S. PATENT DOCUMENTS

| | | | |
|---|---|---|---|
| 2013/0325515 A1* | 12/2013 | Nikolova-Simons | ........................ G16H 10/60 705/3 |
| 2017/0308829 A1 | 10/2017 | Li et al. | |
| 2018/0349557 A1 | 12/2018 | Li et al. | |
| 2019/0034579 A1* | 1/2019 | Day ........................ | G16Z 99/00 |
| 2019/0066836 A1 | 2/2019 | Li et al. | |
| 2021/0018555 A1 | 1/2021 | Haje Obeid et al. | |
| 2022/0293284 A1* | 9/2022 | Gonzales, Jr. ........ | G06F 16/258 |
| 2022/0336088 A1* | 10/2022 | Thomas ................. | G16H 50/20 |

OTHER PUBLICATIONS

Notification of Transmittal of the International Search Report and the Written Opinion of the International Searching Authority from corresponding PCT/US2025/016556 dated May 2, 2025.

* cited by examiner

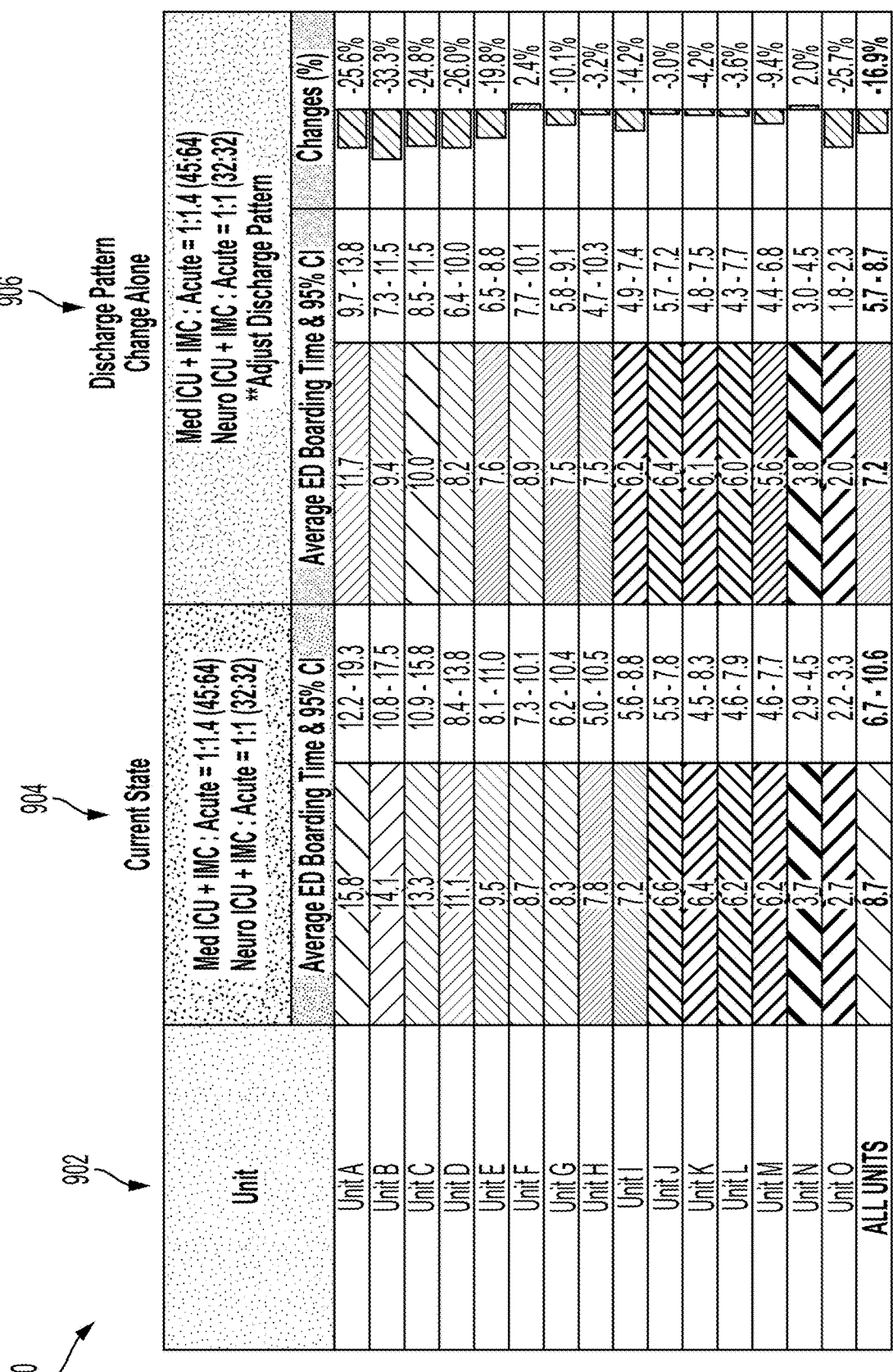

| Unit | Current State<br>Med ICU + IMC : Acute = 1:1.4 (45:64)<br>Neuro ICU + IMC : Acute = 1:1 (32:32) | | Discharge Pattern Change Alone<br>Med ICU + IMC : Acute = 1:1.4 (45:64)<br>Neuro ICU + IMC : Acute = 1:1 (32:32)<br>**Adjust Discharge Pattern | | Changes (%) |
|---|---|---|---|---|---|
| | Average ED Boarding Time & 95% CI | | Average ED Boarding Time & 95% CI | | |
| Unit A | 15.8 | 12.2 - 19.3 | 11.7 | 9.7 - 13.8 | -25.6% |
| Unit B | 14.1 | 10.8 - 17.5 | 9.4 | 7.3 - 11.5 | -33.3% |
| Unit C | 13.3 | 10.9 - 15.8 | 10.0 | 8.5 - 11.5 | -24.8% |
| Unit D | 11.1 | 8.4 - 13.8 | 8.2 | 6.4 - 10.0 | -26.0% |
| Unit E | 9.5 | 8.1 - 11.0 | 7.6 | 6.5 - 8.8 | -19.8% |
| Unit F | 8.7 | 7.3 - 10.1 | 8.9 | 7.7 - 10.1 | 2.4% |
| Unit G | 8.3 | 6.2 - 10.4 | 7.5 | 5.8 - 9.1 | -10.1% |
| Unit H | 7.8 | 5.0 - 10.5 | 7.5 | 4.7 - 10.3 | -3.2% |
| Unit I | 7.2 | 5.6 - 8.8 | 6.2 | 4.9 - 7.4 | -14.2% |
| Unit J | 6.6 | 5.5 - 7.8 | 6.4 | 5.7 - 7.2 | -3.0% |
| Unit K | 6.4 | 4.5 - 8.3 | 6.1 | 4.8 - 7.5 | -4.2% |
| Unit L | 6.2 | 4.6 - 7.9 | 6.0 | 4.3 - 7.7 | -3.6% |
| Unit M | 6.2 | 4.6 - 7.7 | 5.6 | 4.4 - 6.8 | -9.4% |
| Unit N | 3.7 | 2.9 - 4.5 | 3.8 | 3.0 - 4.5 | 2.0% |
| Unit O | 2.7 | 2.2 - 3.3 | 2.0 | 1.8 - 2.3 | -25.7% |
| ALL UNITS | 8.7 | 6.7 - 10.6 | 7.2 | 5.7 - 8.7 | -16.9% |

FIG. 9A

| Transfers: ICU to Acute ICU to IMC IMC to Acute | Current State 954 Med ICU + IMC : Acute = 1:1.4 (45:64) Neuro ICU + IMC : Acute = 1:1 (32:32) | Discharge Pattern Change Alone 956 Med ICU + IMC : Acute = 1:1.4 (45:64) Neuro ICU + IMC : Acute = 1:1 (32:32) **Adjust Discharge Pattern | |
|---|---|---|---|
| | Median Transfer Wait Time | Median Transfer Wait Time | Changes (%) |
| Unit B to D | 13.9 | 12.7 | -8.3% |
| Unit O to D | 11.8 | 10.2 | -13.7% |
| Unit H to C | 10.1 | 6.8 | -33.1% |
| Unit O to B | 7.7 | 7.7 | 0.1% |
| Unit H to G | 7.4 | 6.1 | -18.1% |
| Unit G to F | 6.1 | 5.5 | -10.5% |
| Unit G to C | 4.7 | 4.2 | -11.1% |
| ALL TRANSFERS | 8.8 | 7.6 | -14.0% |

SYSTEM AND METHOD FOR IMPROVING PATIENT TREATMENT

BACKGROUND

At least one example in accordance with the present disclosure relates generally to improving patient medical outcomes, such as in a hospital setting.

SUMMARY

Examples of the methods and systems discussed herein are not limited in application to the details of construction and the arrangement of components set forth in the following description or illustrated in the accompanying drawings. The methods and systems may be capable of implementation in other embodiments and of being practiced or of being carried out in various ways. Examples of specific implementations are provided herein for illustrative purposes and are not intended to be limiting. Acts, components, elements, and features discussed in connection with any one or more examples may be configured to operate and/or be implemented in a similar role in any other examples.

The phraseology and terminology used herein is for the purpose of description. References to examples, embodiments, components, elements, or acts of the systems and methods herein referred to in the singular may also embrace embodiments including a plurality. Similarly, references in plural to embodiments, components, elements, or acts may be implemented as a singularity. References in the singular or plural form may therefore not be intended to limit the presently disclosed systems or methods, their components, acts, or elements. The use herein of "including," "comprising," "having," "containing," "involving," and variations so forth, may encompass the items listed thereafter and equivalents thereof as well as additional items.

References to "or" may be construed as inclusive so that any terms described using "or" may indicate any of a single, more than one, and all of the described terms. For example, the phrase "at least one of A or B" may refer A and/or B—that is, A only, B only, or A and B together. In addition, in the event of inconsistent usages of terms between this document and documents incorporated herein by reference, the term usage in the incorporated documents is supplementary to this document. For irreconcilable differences, the term usage in this document controls.

According to at least one aspect of the present disclosure, a method of operating a patient-discharge-optimization system to improve medical outcomes is provided, the method comprising: accessing, from memory and/or storage, historical patient flow information including a plurality of timestamped events for each patient of a plurality of patients; converting, by the discharge-optimization system, the historical patient flow information into standardized flow information having a standardized format defined by a plurality of standardized parameters; generating, by the discharge-optimization system, a plurality of models, each model indicating an effect of modifying at least one parameter of the plurality of standardized parameters for each patient of the plurality of patients; deriving, by the discharge-optimization system and based on the plurality of models, an optimal discharge histogram for one or more days; forecasting, based on the historical patient flow information, an anticipated future number of discharges for the one or more days; deriving an optimal patient discharge timetable for the one or more days; and providing the optimal patient discharge timetable to one or more users.

In at least one example, the historical patient flow information is stored in the memory and/or storage in a non-standardized format. In at least one example, the method includes storing, by the discharge-optimization system after converting the non-standardized historical patient flow information into the standardized flow information, the standardized flow information in the standardized format in the memory and/or storage. In at least one example, the method includes receiving, from the one or more users, patient discharge information indicative of a deviation from the optimal patient discharge timetable. In at least one example, the method includes automatically updating the optimal patient discharge timetable based on the deviation from the optimal patient discharge timetable responsive to receiving the patient discharge information.

In at least one example, the method includes transmitting a message indicative of updating the optimal patient discharge timetable to a plurality of users over a computer network in real-time so that each user of the plurality of users has immediate access to up-to-date patient information. In at least one example, deriving the optimal patient discharge timetable includes determining, for each day of the one or more days, a number of patients to be discharged on each day and a respective window of time for each patient during which to discharge the respective patient. In at least one example, the optimal discharge histogram indicates an optimal relative frequency to discharge patients for each window of time of a plurality of windows of time within a day. In at least one example, deriving the optimal patient discharge timetable for the one or more days includes deriving, for each hospital unit in a hospital including a plurality of units, a respective optimal patient discharge timetable for each day of the next week.

Examples of the disclosure include at least one non-transitory computer-readable medium storing thereon sequences of computer-executable instructions for operating a discharge-optimization system, the sequences of computer-executable instructions including instructions that instruct at least one processor to: access historical patient flow information including a plurality of timestamped events for each patient of a plurality of patients; convert the historical patient flow information into standardized flow information having a standardized format defined by a plurality of standardized parameters; generate a plurality of models, each model indicating an effect of modifying at least one parameter of the plurality of standardized parameters for each patient of the plurality of patients; derive, based on the plurality of models, an optimal discharge histogram for one or more days; forecast, based on the historical patient flow information, an anticipated future number of discharges for the one or more days; derive an optimal patient discharge timetable for the one or more days; and provide the optimal patient discharge timetable to one or more users.

In at least one example, the historical patient flow information is stored in a non-standardized format. In at least one example, the instructions further instruct the at least one processor to store, after converting the non-standardized historical patient flow information into the standardized flow information, the standardized flow information in the standardized format in the memory and/or storage. In at least one example, the instructions further instruct the at least one processor to receive, from the one or more users, patient discharge information indicative of a deviation from the optimal patient discharge timetable. In at least one example, the instructions further instruct the at least one processor to automatically update the optimal patient discharge timetable based on the deviation from the optimal patient discharge timetable responsive to receiving the patient discharge information.

In at least one example, the instructions further instruct the at least one processor to transmit a message indicative of updating the optimal patient discharge timetable to a plurality of users over a computer network in real-time so that each user of the plurality of users has immediate access to up-to-date patient information. In at least one example, deriving the optimal patient discharge timetable includes determining, for each day of the one or more days, a number of patients to be discharged on each day and a respective window of time for each patient during which to discharge the respective patient. In at least one example, the optimal discharge histogram indicates an optimal relative frequency to discharge patients for each window of time of a plurality of windows of time within a day. In at least one example, deriving the optimal patient discharge timetable for the one or more days includes deriving, for each hospital unit in a hospital including a plurality of units, a respective optimal patient discharge timetable for each day of the next week.

Examples of the disclosure include a discharge-optimization system comprising: at least one graphical user interface; and at least one controller configured to: access historical patient flow information including a plurality of time-stamped events for each patient of a plurality of patients; convert the historical patient flow information into standardized flow information having a standardized format defined by a plurality of standardized parameters; generate a plurality of models, each model indicating an effect of modifying at least one parameter of the plurality of standardized parameters for each patient of the plurality of patients; derive, based on the plurality of models, an optimal discharge histogram for one or more days; forecast, based on the historical patient flow information, an anticipated future number of discharges for the one or more days; derive an optimal patient discharge timetable for the one or more days; control the at least one graphical user interface to display the optimal patient discharge timetable to one or more users; receive, from the one or more users, patient discharge information indicative of a deviation from the optimal patient discharge timetable; and automatically updating, in real-time, the graphical user interface based on the deviation from the optimal patient discharge timetable. In at least one example, the historical patient flow information is stored in a non-standardized format.

BRIEF DESCRIPTION OF THE DRAWINGS

Various aspects of at least one embodiment are discussed below with reference to the accompanying figures, which may not be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or substantially similar component that is illustrated in various figures may be represented by a like numeral. For purposes of clarity, not every component may be labeled in every figure. In the figures:

FIG. 9A illustrates a boarding-time table indicating boarding times in various units within a hospital.

DETAILED DESCRIPTION

Hospitals may treat hundreds to thousands of patients every month. Many hospitals include several different units specializing in various types of procedures. For example, a hospital may include an organ-transplant unit, a general medicine unit, a trauma unit, a pediatrics unit, and so forth. Large hospitals may have dozens of discrete units.

Figure 1:
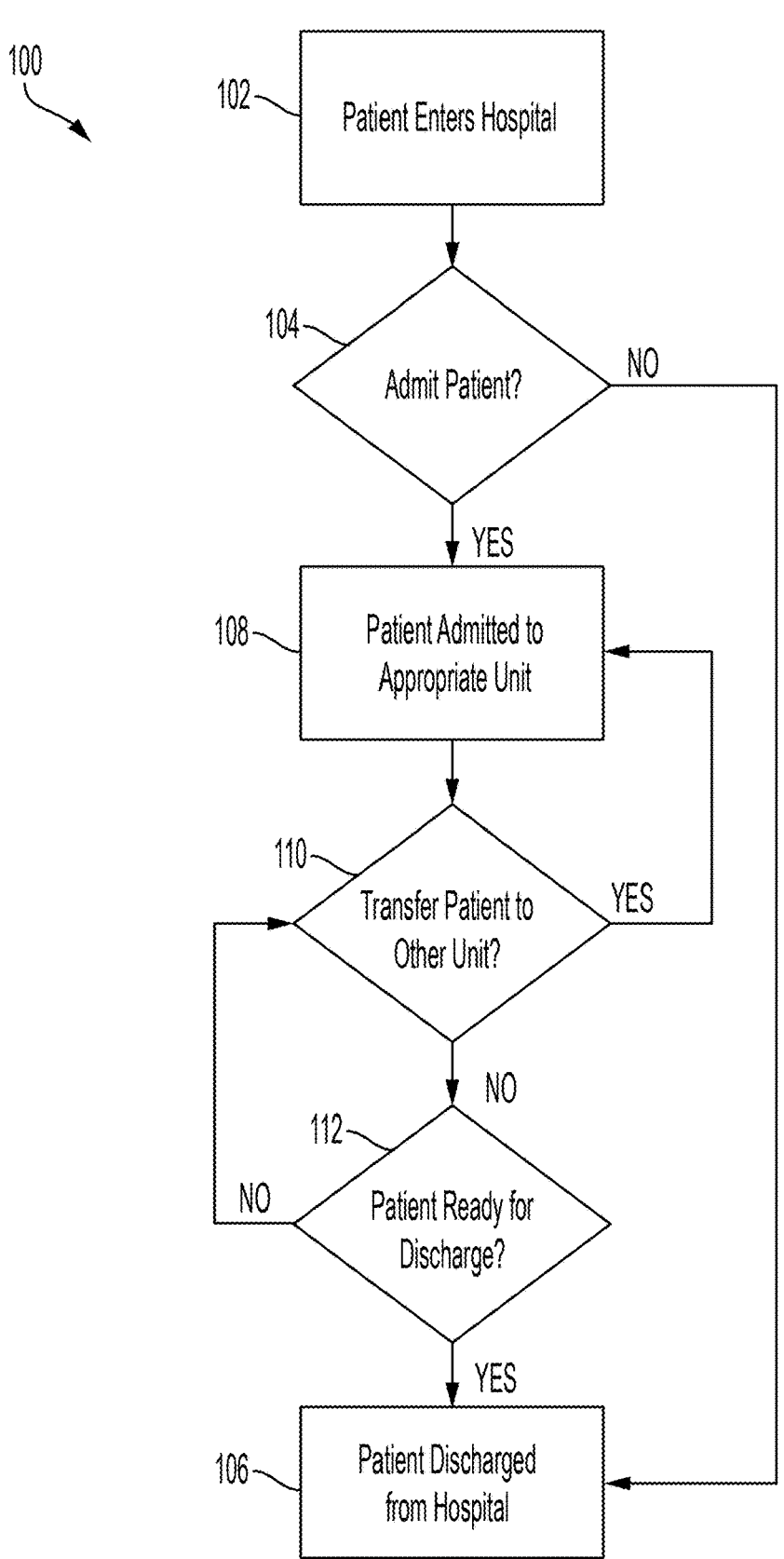
FIG. 1 illustrates a flowchart of a patient's journey throughout a hospital system.

FIG. 1 illustrates a flowchart 100 depicting a patient's potential journey throughout a hospital system. At act 102, a patient first arrives at a hospital. Patients may first arrive at the hospital from any of various initial entry points. For example, a patient may independently arrive at a hospital's emergency department seeking treatment for a medical issue. In another example, a patient may be directly admitted by a doctor without first being seen in the emergency department. For example, a doctor may examine a patient outside of an emergency department (for example, by a doctor in the same hospital, or by a doctor in a different hospital) and may decide that the patient should be admitted to the hospital for further treatment or monitoring. In still other examples, a patient may arrive at the hospital through an operating-room (or "OR") unit of the hospital, such as for elective or emergency surgery. Irrespective of which pathway patients arrive at the hospital, the inflow of patients (including the number of patients and their arrival times) is random (or stochastic).

Intake personnel may collect intake information from the patient at act 102, such as the patient's age, medical history, and a description of the issue that brought the patient to the hospital. Intake personnel may use the intake information to determine whether to admit the patient to the hospital or discharge the patient from the hospital. Intake personnel may input the intake information into an electronic medical record system. Intake procedures may vary depending on how the patient arrives at the hospital. For example, if a patient arrives at the hospital via the emergency department with an extremely urgent medical issue, the patient may be treated immediately without all intake information being first collected.

At act 104, intake personnel determine whether to admit or discharge the patient. If the intake personnel determine that the patient does not need to be admitted to the hospital (104 NO), then the process 100 proceeds to act 106. For example, the intake personnel may determine that the patient does not need to be admitted to the hospital if the issue that brought the patient to the hospital does not require medical attention or does not require further medical attention. Such a situation may arise where, for example, a patient arrives at a hospital via the emergency department, and medical personnel address the patient's medical issue without needing to admit the patient. For example, a patient may receive stitches for a laceration, and may then be free to leave the hospital without being admitted.

At act 106, the patient is discharged from the hospital. Discharging the patient may include the hospital performing the steps to formally release the patient from the hospital, such as providing follow-up instructions to the patient and making applicable notes in an electronic medical record system. The patient may then leave the hospital.

Conversely, if the patient is admitted to the hospital (104 YES), then the process 100 continues to act 108.

At act 108, the intake personnel admit the patient to an appropriate unit of the hospital. For example, if the patient needs an organ transplant, then the patient may be transferred to the organ-transplant unit. If the patient is experiencing a heart-related issue, the patient may be transferred to a cardiac unit, and so forth. In some cases, the patient may be seen by an appropriate medical professional as soon as the patient is admitted to the appropriate unit.

For example, suppose that a patient arrives at an emergency department of a hospital experiencing heart palpitations (act 102). Medical personnel (for example, a triage nurse and/or emergency medicine physician) may examine the patient in the emergency department and decide that the patient should be admitted to the cardiac unit of the hospital so that a cardiologist can examine the patient (act 104). In some cases, a cardiologist may immediately examine the patient as soon as the patient is admitted to the cardiac unit.

In other cases, it may not be possible for the patient to be immediately examined. For example, some units have a finite number of beds for patients. If no beds are available in the unit that the patient is admitted to, then the patient may need to wait until a bed is available. While waiting for a bed in the appropriate unit, the patient may be boarded in the emergency department (that is, the patient is assigned a temporary bed in the emergency department) and may or may not receive treatment in the emergency department. This waiting time may be referred to as an emergency department boarding time. Causing a patient to wait for an available bed in an assigned unit (for example, the cardiac unit) may extend the patient's total length-of-stay in the hospital, which many patients may dislike.

Furthermore, patient care and medical outcomes may be adversely impacted by increased wait times. For example, a patient's condition may deteriorate while waiting to be seen by a medical professional, or the patient may leave without receiving care. In some examples, the patient may be treated in a suboptimal setting, such as in the emergency department. For example, a patient experiencing heart palpitations may be examined by an emergency medicine physician in the emergency department—even though it may be more appropriate for the patient to be examined by a cardiologist in the cardiac unit—because the cardiac unit has no available beds. Accordingly, reducing an amount of time before a patient receives care may improve patient experience and medical outcomes.

Once the patient has been examined by a medical professional in the appropriate unit (or the patient's condition changes, causing the medical staff to re-evaluate which unit the patient should be in), the process 100 continues to act 110.

At act 110, medical staff may determine whether to transfer the patient to another unit. For example, suppose a patient is admitted to the cardiac unit for heart-related issues. A cardiologist may examine the patient and determine that the patient is in urgent need of emergency surgery and needs to be transferred to the surgery unit of the hospital. If the patient needs to be transferred to another unit (110 YES), then the process 110 returns to act 108. The patient is admitted to the appropriate unit (for example, transferring the patient from cardiology to surgery) and acts 108 and 110 are repeated.

Otherwise, if the patient does not need to be transferred (110 NO), then the process 100 continues to act 112. For example, if the cardiologist determines that the patient's heart issues do not require medical attention from another unit, then the cardiologist may determine that the patient does not need to be transferred to another unit.

At act 112, medical staff may determine whether the patient is ready to be discharged. For example, if the cardiologist determines that the patient is not in need of any further medical attention, then the cardiologist may determine that the patient is ready to be discharged (112 YES). The process 100 then continues to act 106, where the patient is discharged from the hospital. A total length of time that the patient has spent in the hospital from being placed in a hospital unit (act 108) to being discharged (act 106) may be referred to as the patient's total length of stay.

Otherwise, if the cardiologist determines that the patient is not ready to be discharged (112 NO), then the process 100 may return to act 110. For example, the cardiologist may decide to keep the patient in the cardiac unit for monitoring for an additional period of time, or may ask the patient to wait while she consults another cardiologist. Acts 110 and 112 may be repeated until a determination is made that the patient should be transferred to another unit (110 YES) or discharged (112 YES).

Accordingly, many patients are transferred between hospital units several times throughout their stay before being discharged. In some cases, a patient may need to wait some period of time before receiving treatment in a given unit. For example, if the patient is transferred to a unit that has no available beds, then the patient may need to wait until a bed becomes available. A unit may have no available beds because all beds are currently occupied by other patients. These delays may increase the patient's overall length-of-stay in the hospital, which many patients may dislike.

Furthermore, these transfer-waiting times may form bottlenecks that lead to cycles of further delays. Suppose that a hospital has two groups of bed units: acute bed units (that is, beds in standard medical and surgical units) and intensive-care bed units (that is, beds in an intensive-care unit [ICU]). Suppose further that a patient in the ICU is ready to be moved to an acute-care unit (or "downgraded"), but that every acute bed unit is occupied. The patient must therefore wait in an intensive-care bed unit until an acute bed unit is available. Thus, not only must the patient wait unit an acute bed unit is available to be transferred, but the patient is still occupying an intensive-care bed unit while waiting for an acute bed unit. This may lead to compounded delays if all intensive-care bed units are occupied, causing patients who need intensive-care bed units to wait for an available bed. The number of patients transfers and the timing of these transfers between hospital units is random (or stochastic) with time.

In some cases, all beds may be occupied by patients who are not ready to be discharged from the hospital. For example, if a particular unit has 10 beds all occupied by patients that are not ready to be discharged from the hospital, that unit may not be able to accept new patients until an already-admitted patient is ready to be discharged or transferred. That is, even if a medical professional were to examine these 10 patients, the medical professional would determine that none of the patients is ready for discharge.

In many cases, however, patients are simply discharged later than necessary. For example, a patient may be ready to be discharged at 9:00 AM (that is, the patient is in a condition that medical personnel would deem eligible for discharge), yet medical personnel may not begin the discharge process until 12:00 PM. This three-hour period between 9:00 AM and 12:00 PM may be referred to as a "discharge delay." Discharge delays are introduced because patients cannot be discharged until a medical professional has examined a patient or assessed their medical state and deemed the patient ready for discharge. There may be a lag between when a patient would be deemed ready for discharge if they were examined or assessed and when the patient is actually evaluated and deemed ready for discharge.

Such discharge delays reduce bed availability because, until the patient is discharged, the bed is not available for other patients. It may therefore be advantageous to minimize the time between when a patient is medically ready to be discharged and when the patient is actually discharged, that is, the discharge delay. Minimizing this discharge delay may improve patient care by minimizing patients' length-of-stay. Moreover, discharging patients sooner increases bed turnover rates, which reduces the time that other patients spend waiting for available beds (such as emergency department boarding times), which in turn reduces those other patients' lengths-of-stay. Examples of the disclosure reduce discharge delays and improve bed availability by determining optimal times to discharge patients. These times may be optimal inasmuch as discharging at these times minimizes a hospital's emergency department (ED) boarding times, unit-transfer-waiting times, and overall patient length-of-stay. Minimizing the time that a patient spends waiting for care, and the time that the patient spends waiting in the hospital, improves patient experience and improves medical outcomes.

Despite the importance of discharging patients in a timely fashion, many hospitals still have significant discharge delays. These discharge delays may be the result of the extremely complex modeling required to anticipate how many beds will be required (and thus how many discharges need to be performed to make these beds available) throughout the day. Because the inflow of patients to the hospital and the number of patient transfers between hospital units is random (or stochastic), it is not practical for medical professionals to accurately anticipate, using only the human mind or even a pen and paper, how many beds will be required later on. Because medical professionals cannot mentally anticipate how many beds will be required later on, these medical professionals cannot accurately plan ahead by discharging patients at times optimized to fulfill these future bed requirements. Patient treatment and medical outcomes may be impacted by these delays in delivering patient care.

An optimal discharge timetable may address these problems by indicating optimal times at which to discharge patients. An optimal discharge timetable may be designed to optimize bed turnover such that the amount of time that other patients spend waiting for an available bed is minimized. However, determining an optimal discharge timetable may involve complex modeling that is entirely impossible or impractical to perform in the human mind, even with tools such as a pen and paper—or even using some computerized tools, such as calculators. Because this complex modeling is impossible to perform in the mind, many hospitals employ a simple "discharge-before-noon" paradigm. Under this paradigm, hospitals attempt to discharge as many patients as possible before noon, and/or may simply react to current conditions in the hospital. In such reactive systems, hospital personnel may notice, for example, that many or all acute bed units are occupied and thus begin attempting to discharge patients occupying the acute bed units.

This reactive process may compound the delays associated with discharges. Reasons for such compounded delays include delays in physicians writing discharge orders, delays in arranging appropriate transport for patients once they leave the hospital, delays in resolving insurance matters with the patients, delays in arranging appropriate laboratory or radiology tests prior to discharge, delays in placing a patient in skilled nursing facilities or rehabilitation facilities post-discharge, and so forth.

Existing approaches to managing patient discharge are therefore not grounded in the availability of or requirement for beds, nor does the paradigm optimize patient flow in a hospital. Rather, these approaches employ an arbitrary, reactive standard that is used simply because it is easy and comprehendible to implement, whereas the complex modeling required to anticipate how many beds will be needed throughout the day is impossible to perform in the human mind. In other words, the pervasiveness of the discharge-before-noon paradigm and reactive discharging is evidence that it is impossible or impractical to determine an optimal discharge timetable in the human mind, even using pen and paper, because existing solutions are inefficient and lack any objective basis beyond ease of implementation.

Indeed, as discussed in greater detail below, an optimal discharge timetable may consider the probability distribution for factors such as fluctuations in inflow of patients, hospital-unit occupancy and composition, the dynamics of transfers of patients between units, the medical acuity of patients being cared for in each unit, demand for beds in each unit, length-of-stay in each unit, and so forth. Each of these factors may be unique to different hospitals, and may thus be considered on a hospital-by-hospital basis. It is not practical for the human mind to consider and analyze all of these factors to arrive at an optimal solution.

Examples of the disclosure therefore provide systems and methods for improving patient treatment and patients' medical outcomes. In some examples, patient outcomes may be improved by optimizing patient-discharge parameters. Patient-discharge parameters may include, for example, timetables indicating how many patients should be discharged within various windows of time throughout the day. For example, an optimized patient-discharge timetable may indicate how many patients should be discharged between 9:00 AM and 10:00 AM for a given day, how many patients should be discharged between 10:00 AM and 11:00 AM for a given day, and so forth. These timetables may be generated for each unit in a hospital for each day.

Such optimized patient-discharge timetables enable medical professionals to make informed discharge decisions. These timetables provide tangible targets grounded in objective needs in the hospital, such as how many beds are predicted to be needed and thus how many discharges need to be completed to make the necessary beds available. For example, if a team of medical professionals understands that four patients must be discharged by 10:00 AM to ensure that adequate beds are available later in the day, then that team of medical professionals can work to identify four patients who are ready to be discharged by 10:00 AM.

Whereas simple discharge-before-noon paradigms have no basis in the actual objective needs of a hospital—and are employed simply because it is impossible for the human mind to determine optimal discharge deadlines that are grounded in the needs of the hospital—the examples provided herein are based on optimizing patient discharge to increase bed availability, and what discharge timeline should be implemented to accommodate those bed requirements. This may be more advantageous than the discharge-before-noon paradigm, which does not set any specific discharge targets and which does not respond to anticipated bed needs. Such a paradigm is at best reactive to a current state of the hospital, but fails to account for historical parameters (for example, a historical number of patients previously cared for at the same time a year prior). Although the discharge-before-noon paradigm is used as one example, similar paradigms which exhibit similar limitations (for example, an inability to respond proactively to a forecasted state of the hospital) are similarly inefficient.

Current systems used to determine patient discharge timing, such as the discharge-before-noon paradigm, are often arbitrary and ineffective at discharging patients at the right times to reduce ED boarding times, the transfer times between hospital units, and the length of stay in hospital units. Such systems may operate inefficiently because patients are discharged later than necessary, creating bottlenecks and increasing patients' overall length-of-stay. Patient care may be delayed by these bottlenecks, leading to adverse medical outcomes. Medical professionals lack the information necessary to make informed decisions as to when to discharge patients, and resort to a simple but inefficient discharge-before-noon paradigm. Medical outcomes for patients are adversely impacted by these inefficient paradigms.

This is a technical problem. An exemplary embodiment of a discharge-optimization system is provided and includes at least one graphical user interface and at least one controller. The at least one controller is configured to access historical patient flow information including a plurality of time-stamped events for each patient of a plurality of patients; convert the historical patient flow information into standardized flow information having a standardized format defined by a plurality of standardized parameters; generate a plurality of models, each model indicating an effect of modifying at least one parameter of the plurality of standardized parameters for each patient of the plurality of patients; derive, based on the plurality of models, an optimal discharge histogram for one or more days; forecast, based on the historical patient flow information, an anticipated future number of discharges for the one or more days; derive an optimal patient discharge timetable for the one or more days; control the at least one graphical user interface to display the optimal patient discharge timetable to one or more users; receive, from the one or more users, patient discharge information indicative of a deviation from the optimal patient discharge timetable; and automatically updating, in real-time, the graphical user interface based on the deviation from the optimal patient discharge timetable.

At least this foregoing combination of features comprises a discharge-optimization system that serves as a technical solution to the foregoing technical problem. Examples of the discharge-optimization system yield demonstrable improvements to discharge systems by demonstrably reducing emergency department boarding times, transfer times between hospital units, and patients' overall length-of-stay. These improvements yield real improvements to medical outcomes and patient care by reducing the time that a patient spends waiting for care. This technical solution is not routine and is unconventional. This technical solution is a practical application of the discharge-optimization system design that solves the foregoing technical problem and constitutes an improvement in the technical field of medical care at least by determining optimal discharge deadlines. These optimal deadlines are grounded in reducing emergency department boarding times, transfer times between hospital units, and patients' length of stay. Conversely, the simple discharge-before-noon paradigm is not grounded in these objective metrics, and is simply more easily implemented and, unlike the examples discussed herein, capable of being performed in the human mind alone or with pen and paper.

This technical solution improves the technical field of medical care by reducing the time that a patient spends waiting for treatment in the appropriate care setting, and thereby yields improvements in patient outcomes. These improvements are not theoretical; as discussed below with respect to FIGS. 9A and 9B, patient wait times can be demonstrably reduced by many hours. By delivering medical treatment to patients hours before they would otherwise receive care, significant improvements to the technical field of medical care may be realized.

For example, consider a patient who comes to the ED complaining of chest pain. Medical personnel may determine that the patient should be admitted to the cardiac unit. However, no beds are available in the cardiac unit, and the patient is boarded in the emergency department while waiting. The patient receives care in the emergency department, but the care may not be optimal based on the patient's condition. The patient may be examined by an emergency-medicine physician in the emergency department, who does not specialize in cardiac issues like a cardiologist does. Moreover, the emergency department may not have all of the specialized cardiac telemetry equipment that the physician may need, but which may be in the cardiac unit rather than the emergency department. If the patient were instead seen by a cardiologist and cared for by a team of healthcare professionals who are appropriately trained to manage and treat patients with potential cardiac issues, the patient may receive better care. Due to delays in getting this patient the appropriate care by the appropriate medical professionals in the correct setting (for example, the cardiac telemetry unit instead of the emergency department due to the unavailability of a bed in the cardiac unit), this patient may die.

In another example, a patient may develop an infection or sepsis while admitted to the hospital. Physicians in the emergency department may not immediately realize that the patient has developed sepsis, because the emergency department is hectic and physicians' attention may be diverted elsewhere. The patient's sepsis may become worse the longer it remains unnoticed and/or untreated. Depending on the severity, sepsis can be life-threatening. The risk of mortality dramatically increases with the severity of the infection. If the case of sepsis is severe, the patient may need to be transferred to the ICU for appropriate escalation of care. Delays in transferring patients to the ICU, which is better equipped to manage patients in this condition, could lead to organ failure, tissue damage and death.

In another example, a patient undergoes surgery and is brought to the Post-Anesthesia-Care Unit (PACU) for anesthesia-related recovery. The PACU may be intended for patients who are still unconscious from the effects of anesthesia. Once patients awaken in the PACU, physicians in the PACU may examine the patient and transfer the patient to an appropriate unit (for example, the surgical unit) if the patient is not experiencing any post-anesthesia complications. In this example, however, the surgical unit may not have any available beds. Due to the lack of availability of beds in the surgical unit in an example, the patient cannot be moved to the unit and may stay in the PACU overnight. After being in the PACU for over eight hours, the patient develops upper respiratory complications and begins to rapidly deteriorate. As a result, the patient is intubated to allow the patient to breathe. While the patient is eventually stabilized and ultimately transferred to a surgical unit, the patient's length of stay in the hospital increases due to the upper respiratory event and intubation, leading to a longer recovery time and greater healthcare cost to the patient.

Figure 2:
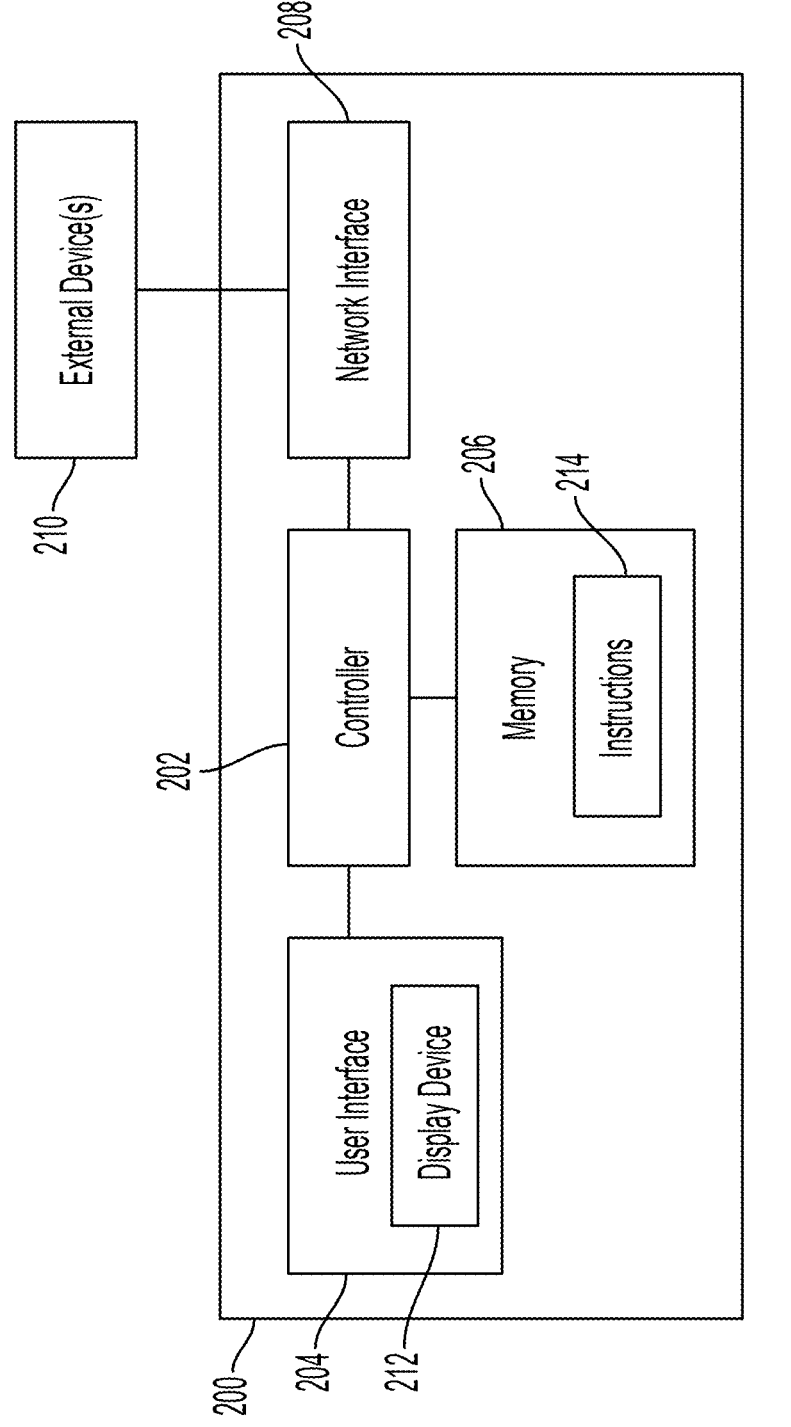
FIG. 2 illustrates a block diagram of a discharge-optimization system according to an example.

In various examples, a patient-discharge-optimization system (or "discharge-optimization system") may include one or more computing devices. FIG. 2 illustrates a block diagram of a discharge-optimization system 200 according to an example. The discharge-optimization system 200 includes at least one controller 202 ("controller 202"), at least one user interface 204 ("user interface 204"), memory and/or storage 206 ("memory 206"), and at least one network interface 208 ("network interface 208"). The discharge-optimization system 200 may be coupled to one or more external devices 210 ("external devices 210") via the network interface 208.

Medical personnel, such as the personnel tasked with discharging patients, may use the discharge-optimization system 200 to aid in discharging patients. As discussed in greater detail below with respect to FIG. 4, the discharge-optimization system 200 may aid medical personnel by generating optimal discharge timetables for the medical personnel to implement. For example, the controller 202 may generate the optimal discharge timetable based on information stored in the memory 206, and/or based on information received from the external devices 210, and display the optimal discharge timetable on the user interface 204. For example, the user interface 204 may include a display device 212 (for example, a computer monitor, laptop display, smartphone display, or other such displays) to display the optimal discharge timetable. Accordingly, references to the user interface 204 displaying information may include the display device 212 displaying information. Medical personnel may also input information via the user interface 204, such as real-time information indicative of when patients are actually being discharged. The controller 202 may analyze any differences between the actual discharges and the optimal discharge timetable and automatically update the optimal discharge timetable in real-time based on the differences.

Figure 3A:
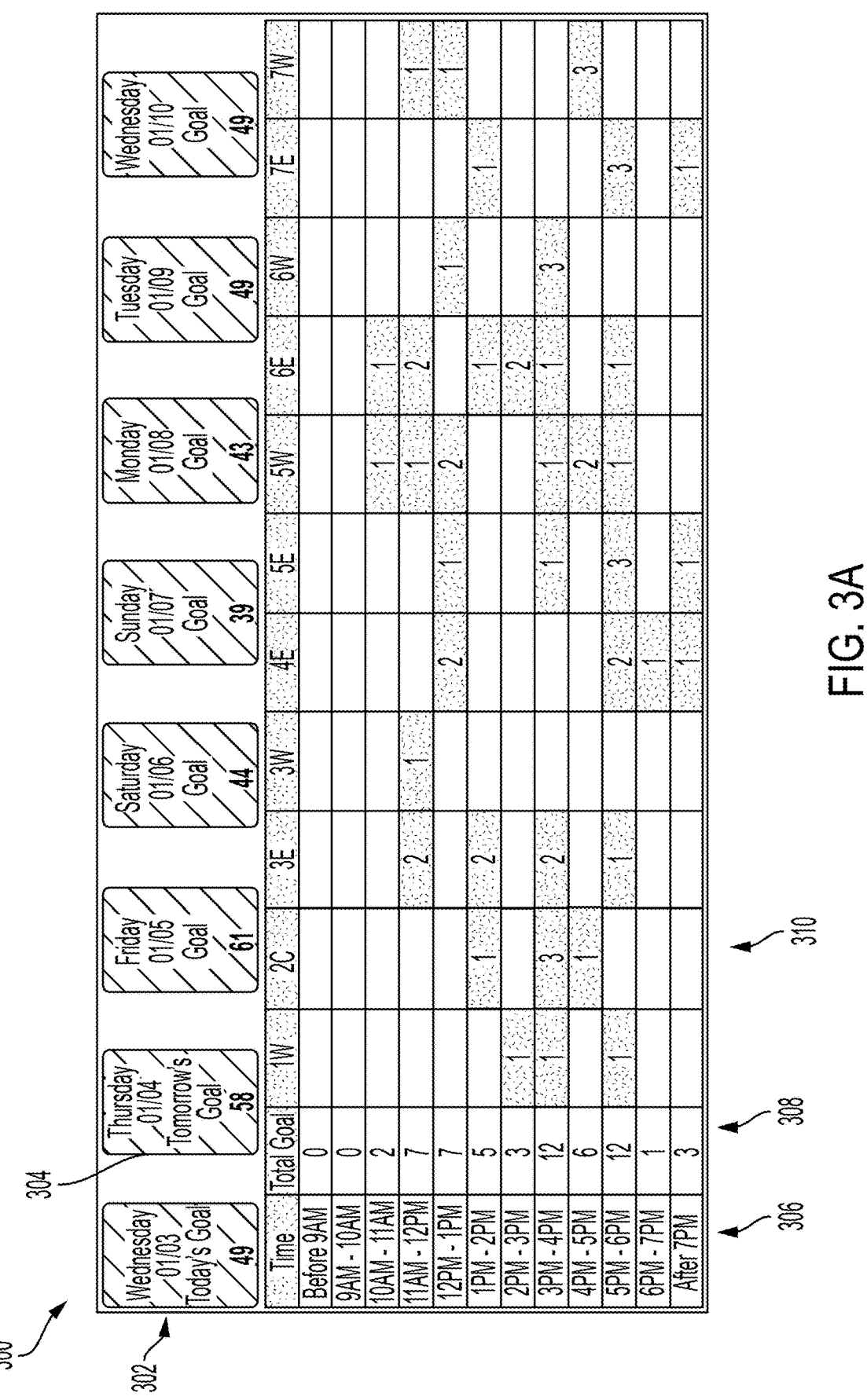
FIG. 3A illustrates a daily optimal discharge timetable for a representative hospital unit according to an example.

FIG. 3A illustrates a daily optimal discharge timetable 300 according to an example. The daily optimal discharge timetable 300 illustrates time windows during which a number of patients should be discharged for each hospital unit for a given day. The controller 202 may generate the daily optimal discharge timetable 300 as discussed below with respect to FIG. 4. The controller 202 may cause the user interface 204 to display the daily optimal discharge timetable 300 to a user, such as medical personnel managing patient discharge. The daily optimal discharge timetable 300 provides the user with specific discharge goals, such as a number of patients to discharge within specified windows of time.

In some examples, the daily optimal discharge timetable 300 may be available to medical personnel several days in advance. For example, a daily optimal discharge timetable 300 may be generated a week before the actual day that is the subject of a given timetable. Medical personnel may therefore have several days' advance notice of daily discharge goals, which enables the medical personnel to execute a discharge plan for meeting the daily discharge goals.

By providing the user with specific, concrete targets designed to accommodate future bed needs, the medical personnel may attempt to proactively identify patients who will be ready to be discharged within the specified windows of time. For example, consider a patient who, from 12:00 PM onwards on the day before actual discharge, would be considered medically ready for discharge if that patient were examined. Under a discharge-before-noon paradigm, medical personnel may not examine the patient until 11:00 AM the next day (that is, on the day of actual discharge) because no concrete target other than "before noon" exists.

However, if the medical personnel knew that a patient should be discharged by, for example, 9:00 AM on a given day, the medical personnel may initiate discharge-preparation activities at an appropriate time to meet the discharge goal (for example, 24-48 hours in advance of the discharge goal of 9:00 AM) for an appropriate patient. For example, the medical personnel may arrange appropriate laboratory or radiology tests required for discharge, place orders for medications the patient may require, and so forth.

The timetable 300 includes a day-select row 302. The day-select row 302 allows a user to select which day to show a discharge timetable for. The day-select row 302 may include any number of days and, in the example of FIG. 3A, includes buttons for each day in the next week. Each button also displays a number of patients to be discharged on that respective day. For example, the day-select row 302 includes a button 304 for Thursday, January $4^{th}$. The button 304 indicates that 58 patients should be discharged on Thursday. In the example of FIG. 3A, a user has selected the button 304, and thus the timetable 300 has been generated for that given Thursday.

The timetable 300 also includes a time column 306. The time column 306 includes windows of time throughout the selected day during which to discharge patients. In some examples, the windows of time may be uniform. For example, each window of time may include the same duration, such as one hour. In other examples, such as the example shown in FIG. 3A, variable windows of time may be implemented. For example, as shown in FIG. 3A, the top of the time column 306 includes a "Before 9 AM" window spanning 12 AM to 9 AM. The bottom of the time column 306 includes an "After 7 PM" window spanning 7 PM to 12 AM. Each other cell in the time column 306 includes a one-hour window, such as a 9 AM to 10 AM window, a 10 AM to 11 AM window, and so forth. In other examples, other time windows may be implemented; the time windows illustrated in FIG. 3A are provided simply for purposes of example.

The timetable 300 also includes a discharge-count column 308. The discharge-count column 308 indicates how many patients should be discharged across all units in a hospital system for a corresponding time window. For example, between 11 AM and 12 PM (indicated by the time column 306), four patients should be discharged (indicated by the discharge-count column 308) across all units.

The remaining columns of the timetable 300 correspond to various units within a hospital. For example, an example unit column 310 corresponds to a "2C" unit on the hospital campus, which may indicate the name of the hospital unit. In particular, "2C" may refer to a central wing ("C") of the second floor ("2") of a building, which may house a collection of beds and other specialized equipment and/or rooms that make up a hospital unit. As indicated in the example unit column 310, one patient should be discharged in the window spanning 1 PM to 2 PM, three patients should be discharged in the window spanning 3 PM to 4 PM, and one patient should be discharged in the window spanning 4 PM to 5 PM. Similar columns are provided for each other hospital unit in the hospital system. In some examples, each cell in the timetable 300 is illustrated with heatmap-style coloring such that a color of each cell is correlated to the number of patients to be discharged. For example, cells corresponding to discharge windows with a greater number of patients to be discharged (for example, three patients) may be shaded with a darker color than cells corresponding to windows with a lesser number of patients to be discharged (for example, one patient).

Figure 3B:
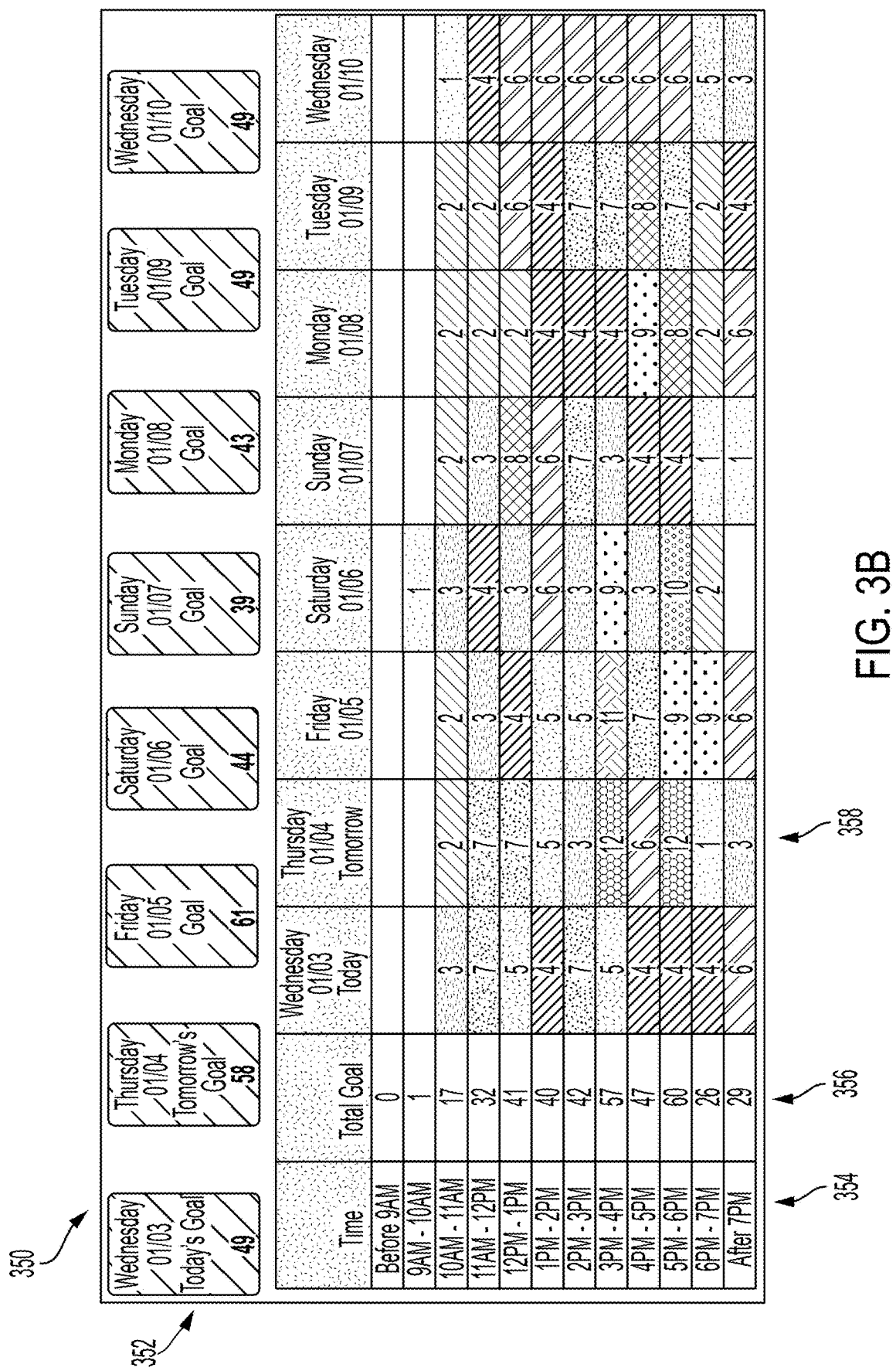
FIG. 3B illustrates a daily optimal discharge timetable for all hospital units in aggregate according to an example.

Similar timetables may be generated for entire hospital systems on a weekly basis. FIG. 3B illustrates a weekly optimal discharge timetable 350 according to an example. The timetable 350 includes a day-select row 352, a time column 354, and a discharge-count column 356, which are similar or identical to the day-select row 302, the time column 306, and the discharge-count column 308, respectively. However, rather than including a discharge count for each unit of a hospital system in each time window for a given day in the remaining columns, the timetable 350 includes discharge counts across all units in a hospital system for each day in the following week.

For example, the timetable 350 includes a daily-discharge-count column 358 corresponding to the discharges for the next day, Thursday, January $4^{th}$, across all units. As indicated by the daily-discharge-count column 358, two patients are to be discharged across the entire hospital system between 10 AM and 11 AM, seven patients are to be discharged across the entire hospital system between 11 AM and 12 PM, seven patients are to be discharged across the entire hospital system between 12 PM and 1 PM, and so forth. It is to be appreciated that the weekly optimal discharge timetable 350 provides data for a week simply for purposes of example, and that timetables may be generated for other durations of time (for example, five days, 10 days, two weeks, and so forth) in other examples.

Accordingly, the timetables 300, 350 provide two examples of discharge timetables that may be provided, via the user interface 204, to medical personnel. Medical personnel may then use the timetables 300, 350 to guide discharge procedures. For example, if medical personnel understand that one patient in the "2C" unit of the hospital should be discharged between 1 PM and 2 PM on Thursday, January $4^{th}$, then the medical personnel can evaluate patients in the 2C unit before 1 PM on Thursday, January 4th, to identify one patient who meets discharge-eligibility criteria. As discussed above, medical personnel may begin this discharge-planning process approximately 24-48 hours in advance to ensure adequate time to arrange tests, order medications, and so forth. The discharged patient's bed may then be prepared for use by other patients later in the day.

As discussed above, the controller 202 may generate the timetables 300, 350 in some examples, and may display the timetables 300, 350 to medical personnel via the user interface 204. In other examples, the external devices 210 may generate timetables such as the timetables 300, 350, and provide the timetables to the discharge-optimization system 200 via the network interface 208. For purposes of example, a process of generating discharge timetables is provided in which the controller 202 generates the timetables. However, in other examples, other computing devices may generate the timetables in addition to, or in lieu of, the controller 202.

Figure 4:
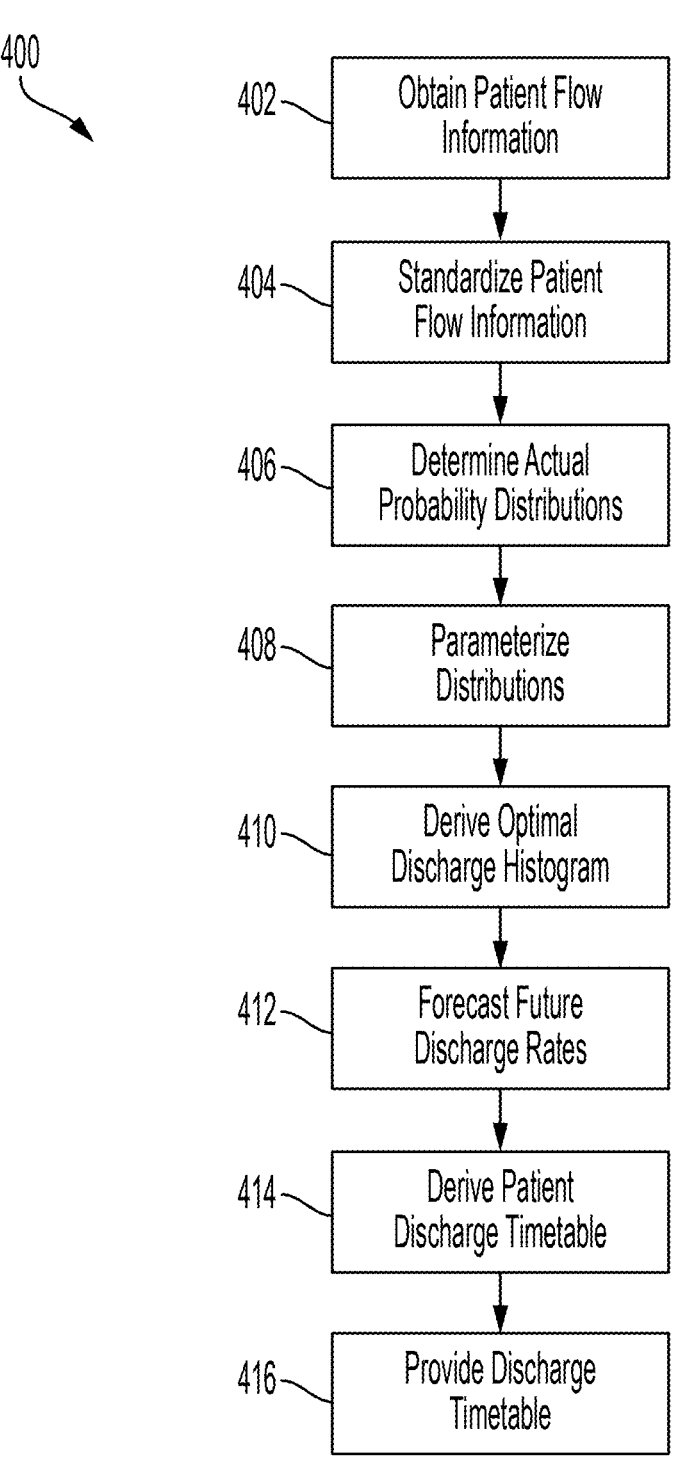
FIG. 4 illustrates a process of generating at least one optimized discharge timetable according to an example.

FIG. 4 illustrates a process 400 of generating at least one optimized discharge timetable according to an example. The process 400 may be executed by the controller 202 in at least one example. As noted above, however, the process 400 may be executed by the external device 210 in addition to, or in lieu of, the controller 202 in other examples.

At act 402, the controller 202 obtains historical patient flow information for each of a plurality of patients who have received care in the hospital over a given period of time. Patient flow information includes information indicative of the flow of each patient throughout a hospital system. This historical patient flow information may be acquired for a large number of patients who previously entered into a given hospital system, and may be used at least for the purpose of modeling how patients are expected to flow throughout a hospital system.

For example, patient flow information may include time-stamped information indicative of when a decision is made to admit the patient to a hospital, when a patient is transferred to a first unit within the hospital, when a patient is transferred to a second unit within the hospital, and so forth. In various examples, medical personnel (for example, intake personnel, a doctor overseeing the patient's care, a nurse administering medication, and so forth) may log this information in an electronic medical record system as the medical personnel care for the patient. This information may be stored in memory and/or storage, such as the memory 206 or the external device 210. As noted above, this patient flow information may include a large body of information for a large number of patients over a large period of time (for example, every patient that a given hospital has served within the past five years).

Figure 5A:
FIG. 5A illustrates a patient-flow graph indicative of relative patient volume flow throughout a hospital according to an example.
Figure 5A:

FIG. 5A illustrates a patient-flow graph 500 indicative of patient flow throughout a hospital according to an example. The patient-flow graph 500 is a Sankey diagram indicating how patients are transferred between hospital units between arrival 502 and discharge 504. A patient may traverse through a plurality of states 506, each corresponding to a respective hospital unit, during their stay. For example, the states 506 include a state for medicine acute units 508 corresponding to the acute medicine unit of the hospital.

Figure 5B:
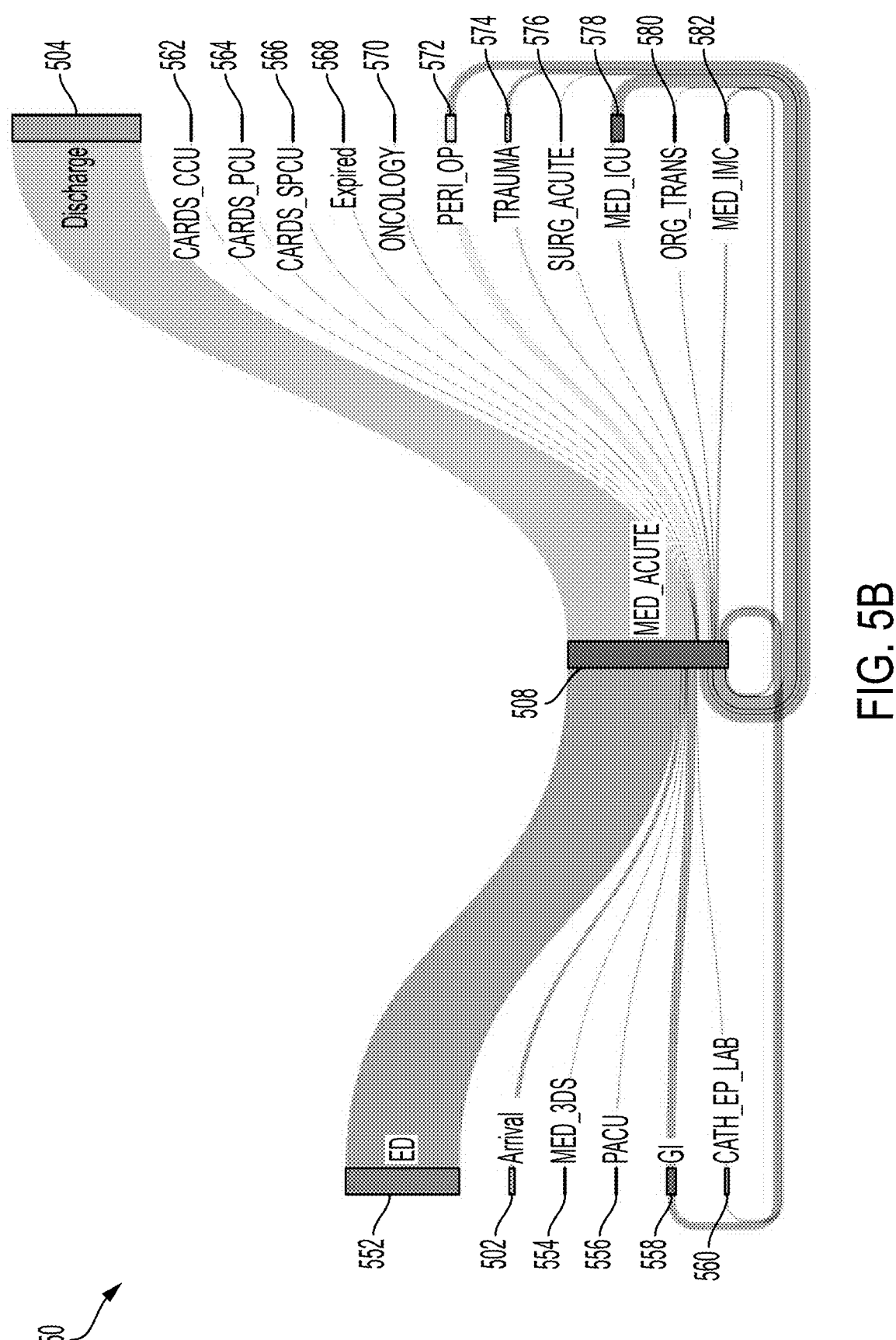
FIG. 5B illustrates a simplified medicine-patient-flow graph indicative of patient flow for a medicine unit according to an example.

To illustrate a specific example of the medicine acute units 508 of the patient-flow graph 500, FIG. 5B illustrates a simplified medicine-unit flow graph 550 depicting patient flow within the medicine acute units 508. The graph 550 represents various patient pathways involving the medicine acute units 508.

A portion of the patients enter the medicine acute units 508 directly upon arrival 502, bypassing any intermediate transfers. Conversely, a significant number of patients are transferred to the medicine acute units 508 from several departments including the emergency department 552, the medicine telemetry department 554, and the PACU 556. Additionally, patients may be transferred from various other departments to the medicine acute units 508, including the Gastrointestinal (GI) unit 558, Cardiac Electrophysiology (EP) Lab 560, perioperative care 572, trauma units 574, surgical acute units 576, medicine Intensive Care Units (ICUs) 578, organ transplant units (580), and Intermediate Care (IMC) units 582.

When leaving the medicine acute units 508, a majority of patients transition from the medicine acute units 508 directly to discharge 504 in the example of FIG. 5B. However, some patients are transferred to other units from the medicine acute units 508 prior to discharge 504. For example, patients record patient events using different, non-standardized formats. The example of Table 1 depicts how the care delivered to the same, hypothetical patient might be recorded differently in the hospitals' EMR systems. An EMR system for a first hospital is referred to as "EMR System A," and is depicted in the middle column of Table 1. An EMR system for a second hospital is referred to as "EMR System B," and is depicted in the right-hand column of Table 1. A classification of care-event types is depicted in the left-hand column of Table 1.

TABLE 1

| | Non-Standardized Patient Flow Information | |
|---|---|---|
| Event Type | First Hospital - EMR System A | Second Hospital - EMR System B |
| Admission | Patient 12345 at 2024 1 Jan. 8:30am Arrival mode: Table X (Ambulance) Acuity level: Table X (Urgent) Level of care: Table Y (Coded level 3) Admission source: Table Y (ED) Admission type: Table Z (Emergency) | John Doe Jan. 1, 2024 08:30:00 ET Arrival mode: Table A (EMS) Acuity level: Table B (3 Grey) Level of care: Table C (Med-Surg) Admission source: Table D (Emergency Dept) Admission type: Table E (Red) |
| Transfer | Patient 23456 at 2024 Jan. 3 9:45am Transferred to unit B, room 700, bed 710-B | John D. Jan. 3, 2024 09:45:00 ET Transferred to location B//700//710-B |
| Discharge | Patient 34567 at 2024 Feb. 4 4:55pm Discharged by Car to Rehab facility with the Spouse for Observation | JD Feb. 4, 2024 16:55:00 ET Leaving hospital with Wife Driving him to XX Center of Maryland for Further Care | may be transferred from the medicine acute units 508 to any of various cardiac care units 562, 564, 566 or to an oncology department 570. Some patients may also expire 568.

Accordingly, patients may flow through various units in a hospital. Patients are often transferred between units. Patient flow information obtained at act 402 includes the corpus of information describing each patient's care throughout the hospital, such as a collection of timestamped information input into an electronic medical record system for each patient. Each timestamped input may indicate an action that was performed in connection with patient care, such as decisions to admit patients to certain units. This corpus of information may be provided for a large number of patients, such as every patient treated by the hospital for the past year or years. In some examples, the patient information may be non-standardized. Different hospitals may employ different electronic medical record (EMR) systems for recording a patient's care, and the non-standardized patient information for one hospital may differ from the non-standardized patient information for another hospital.

At act 404, the controller 202 standardizes the patient flow information. Standardizing the patient flow information may include converting non-standardized patient flow information to standardized patient flow information. As discussed above, non-standardized patient flow information may include a collection of events with associated timestamps. Such events may include, for example, a time at which a decision is made to admit a patient to a hospital, a time at which a decision is made to transfer a patient from one unit to another unit, and so forth. However, different hospitals may implement different EMR systems for tracking patient care. Thus, this patient flow information may not be standardized between hospitals.

For example, Table 1 illustrates examples of how two different hospitals using two different EMR systems might Underlined features of Table 1 may indicate different stored information about a patient. Non-underlined features may be provided for context and may or may not be stored by an actual EMR system. For example, suppose that a patient named John Doe arrives at a hospital via ambulance and is admitted at 8:30 AM. As indicated by the underlined features in the "Admission" row of Table 1, the first hospital may record John Doe's admission by assigning John Doe a patient-identification number (12345). The first hospital may record a time of admission in a YYYY/M/D date format and an H:MM PM/AM time format. Conversely, the second hospital may record John Doe's name (rather than a patient-identification number) and may record a time of admission in a M-D-YYYY date format with an HH:MM:SS time format. Thus, while both hospitals are recording the same type of event (a patient arriving at a particular time), the different EMR systems record the event differently.

Each hospital may record John Doe's arrival mode and acuity level differently. The first hospital may choose a mode of arrival and acuity level from a predefined list of options in a table, Table X. The first hospital may record the patient's mode of arrival as "Ambulance," and may record the patient's acuity level as "Urgent," both options being selected from the list of options in Table X. Conversely, the second hospital may consult one table, Table A, to choose the mode of arrival as emergency medical services ("EMS"), and may consult another table, Table B, to choose the acuity level as "3 Grey," which represents a number-and-color code. The acuity level of "3 Grey" may be selected using an internal naming convention specific to the second hospital, where "3 Grey" has a meaning that only personnel in the second hospital would understand. Although "3 Grey" may have the same meaning as "urgent" in the first hospital's terminology, the different EMR systems record the event differently.

Each hospital may then record John Doe's level of care and admission source differently. The first hospital may choose a level of care and admission source from a pre-defined list of options in a table, Table Y. The first hospital may record John Doe's level of care as "Coded level 3," which may represent an internal naming convention familiar only to personnel within the first hospital, and may record John Doe's admission source as being from the emergency department ("ED"). Conversely, the second hospital may consult one table, Table C, to record the level of care as being medical-surgical ("Med-Surg"), and may consult another table, Table D, to record the admission source as "Emergency Dept."

Each hospital may then record John Doe's admission type differently. The first hospital may choose an admission type from a predefined list of options in a table, Table Z. The first hospital may record John Doe's admission type as "Emergency." The second hospital may choose an admission type from a predefined list of options in a different table, Table E. The second hospital may record John Doe's admission type as "Red." Although "Red" may have the same meaning as "Emergency" in the second hospital's terminology, the different EMR systems record the event differently.

Accordingly, even in admitting a patient to a hospital, different hospitals may record events for the same patient receiving the same care differently. Because of this non-standardization of different hospitals' EMR systems, medical personnel from the first hospital may not be able to understand care information stored in the second hospital's EMR system. Similar principles may apply to how different EMRs track transfers and discharges.

For example, suppose that a patient, again named John Doe, is transferred to a unit "B," in room "700," to bed "710-B," at 9:45 AM. As indicated by the underlined features of the "Transfer" row of Table 1, the first hospital may assign John Doe (who may be a different patient than the "John Doe" assigned patient-identification number "12345") a patient-identification number of "23456," and may record the time of transfer in a YYYY:M:D date format, with a H:MM AM/PM time format. The first hospital may record the transfer location as being to unit "B," in room "700," to bed "710-B." Conversely, the second hospital may not assign John Doe an identification number, and may record his name as "John D." The second hospital may record the time of transfer in a M-D-YYYY date format, with a HH:MM:SS time format. The second hospital may record John Doe's transfer location as "B//700//710-B," which represents a single string combining unit, room, and bed information.

Recording events associated with patient discharge may also differ between EMR systems. For example, suppose that a patient, again named John Doe, is discharged at 4:55 PM. John Doe may be discharged so that John Doe's wife can drive him to a rehabilitation facility for further care and/or observation at the XX Center of Maryland. The first hospital may assign John Doe (who may be different than the John Does assigned patient-identification numbers "12345" and "23456") a patient-identification number of "34567," and may record the time of discharge in a YYYY/M/D date format with a H:MM:SS AM/PM time format. The first hospital may record the details of John Doe's discharge as being released to his "Spouse," so that she may drive John Doe via "Car" to a "Rehab facility" for "Observation." Conversely, the second hospital may record the details of John Doe's discharge as being released to his "Wife," so that she "Driv[e]" him to the "XX Center of Maryland" for "Further Care."

Accordingly, different hospitals may use different EMR systems to store and record patient flow information. Even if the same hypothetical patient were to receive the same exact type of care at the same time, different hospitals may track the patient's care with entirely different recording approaches. Thus, the data stored in EMR systems is non-standardized across different hospitals. Act 404 may therefore include the controller 202 standardizing the non-standardized patient flow information.

Standardizing the patient flow information may include using the non-standardized timestamp information to determine, for each patient, a standardized sequence of patient-stay durations at each leg along the patient's journey. Each standardized sequence may be defined by one or more parameters, such as a total length of stay, a total length of time in each particular unit the patient was in, a total boarding time in one or more units, a total transfer-waiting time in each unit, and so forth.

Each leg may be defined between two discrete events. These events may include, for example, a patient's arrival, an inpatient admission, a bed request to a unit (that is, a request that the patient be moved to a bed in a given unit), transfers to and from units, a time of discharge, and so forth. In some examples, each leg may be defined between two events or more. The events may be consecutive or non-consecutive. For example, a leg of consecutive events may be a total time in a particular unit, and may span from a timestamp of the patient's arrival in that unit to a timestamp of the patient's departure from that unit. Between arrival in that unit and departure from that unit, the patient may (or may not) be associated with intervening timestamped events, such as looping transfers between other units. A leg of non-consecutive events may be a total length-of-stay for the patient, and may span from a timestamp of the patient's arrival to a timestamp of the patient's time of discharge. These events may not be consecutive if, for example, intervening events such as transfers between units are recorded.

In some hospitals, hundreds of thousands of legs may exist throughout the hospital. Each of these legs corresponds to a different combination of movements of patients to, from, and between hospital units or hospital locations (for example, operating rooms, procedure locations, and so forth) between patient admission and patient discharge. Accordingly, a number of potential legs throughout a hospital may increase exponentially with the number of units in a hospital.

The standardized information may include a collection of these legs for each individual patient. That is, at act 404, patient information for each individual patient may be separately standardized to generate an individualized collection of legs for each respective patient. For example, suppose that the non-standardized patient flow information acquired at act 402 for a given patient includes a series of time stamps indicating that a patient arrived at intake at 1 AM, was admitted to a first unit in the hospital at 3 AM, was transferred to a second unit at 10 AM, was transferred back to the first unit at 4 PM, and finally was discharged at 10 PM. Standardizing this patient flow information may include converting this non-standardized patient flow information into a standardized sequence of patient-stay legs or sequences, including a first sequence from 1 AM to 3 AM in intake, a second sequence from 3 AM to 10 AM in the first unit, a third sequence from 10 AM to 4 PM in the second unit, and a fourth sequence from 4 PM to 10 PM back in the first unit until the patient is discharged. Additional sequences may also be determined, such as a total length-of-stay sequence corresponding to 1 AM to 10 PM.

This standardized information may be generated for each patient. For example, the standardized information may be generated for each patient that has been treated in the hospital for a past period of time, such as the past year, past five years, the past number of years since the hospital began implementing an electronic medical record system, and so forth. Because the information is standardized to durations of time in and between units, the flow of every patient through the hospital may be collectively analyzed to determine a probability distribution for patients' journeys throughout the hospital derived from the standardized information, as discussed with respect to act 406.

To generate the standardized information including a collection of legs between discrete events, the differently stored events indicated by the non-standardized patient flow information (for example, as stored in a hospital's EMR system) may be converted into standardized discrete events. As discussed above, different hospitals may use different EMR systems to record the same care in different ways. Act 404 may therefore include converting the non-standardized patient flow information into standardized patient flow information by establishing standardized discrete patient-care events, and determining the legs between one or more discrete events.

Standardizing the non-standardized patient flow information may include converting the non-standardized patient flow information into a standardized format. Table 2 illustrates an example of how the non-standardized information presented in Table 1 in two different formats may be represented in a standardized format according to an example.

facility—in particular, some unspecified institution not selected from a pre-populated list of institutions, because the "XX Center of Maryland" is a fictional institution used only for purposes of example in this disclosure—and that the patient is being driven by the patient's spouse to the institution for purposes of observation.

Accordingly, act 404 may include converting non-standardized patient flow information (for example, as illustrated in Table 1) into standardized patient flow information (for example, as illustrated in Table 2) defined by various standardized parameters which make up certain discrete events, such as admission events, discharge events, and/or transfer events. Act 404 may also include determining one or more legs between pairs of discrete events to define a patient's journey throughout a hospital. For example, in Table 1, a first leg may be established between the admission event and the transfer event, and a second leg may be established between the transfer event and the discharge event. These legs may also be considered standardized parameters.

At act 406, the controller 202 determines actual probability distributions for patient flow throughout the hospital. Generating the model may include aggregating the standardized patient flow information determined at act 404. Each probability density function may indicate a density function of the length of time that a patient may spend during a respective leg of their hospital stay.

Figure 6A:
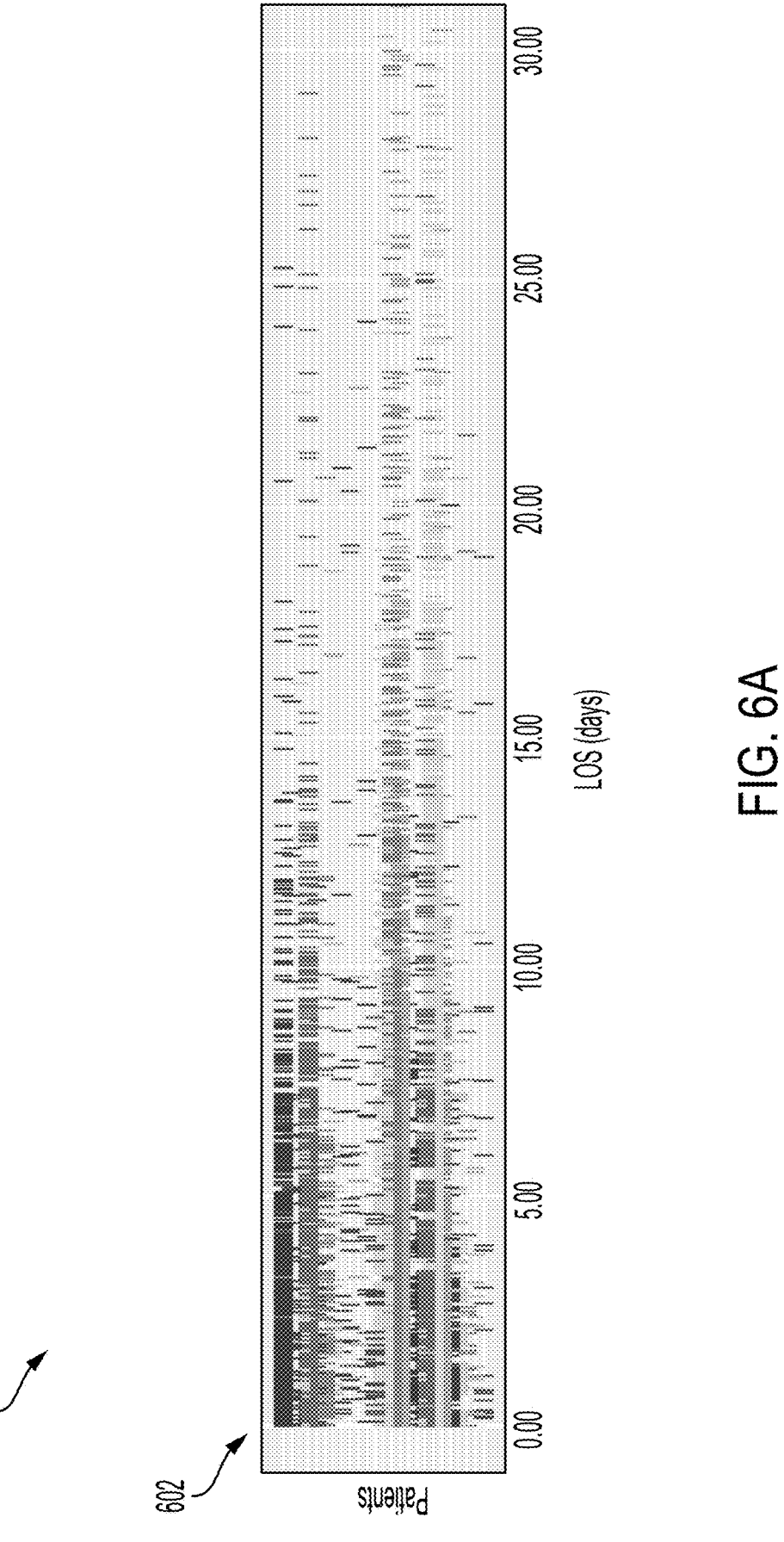
FIG. 6A illustrates a graph of an observed length-of-stay according to an example.

For example, FIG. 6A illustrates a graph 600 of an observed length-of-stay according to an example. As discussed above, the standardized information may include a standardized length-of-stay metric for each observed patient. The graph 600 includes a plurality of rows 602 of data points, each row indicating an observed length-of-stay in a respective hospital unit.

TABLE 2

| | | | | Standardized Patient Flow Information |
|---|---|---|---|---|
| Patient ID | Visit ID | Event Type | Record Time | Details |
| 12345 | 987654 | Admission | 2024 Jan. 1 8:30 | Ambulance A County EMS\|3H Grey Med-Surg (Med-Surg WITHOUT Telemetry)\|Home, Self Referred, Group Home, Congreg House, Foster\|Emergency |
| 23456 | 876543 | Transfer | 2024 Jan. 3 9:45 | Unit B\|Nursing Units\|Room 700\|Bed 710-B\|Med-Surg (Med-Surg WITHOUT Telemetry)\|47983701 |
| 34567 | 765432 | Discharge | 2024 Feb. 4 16:55 | Car\|Rehab Facility\|Other Unspec Instit\|Spouse\|Observation |

Figure 6B:
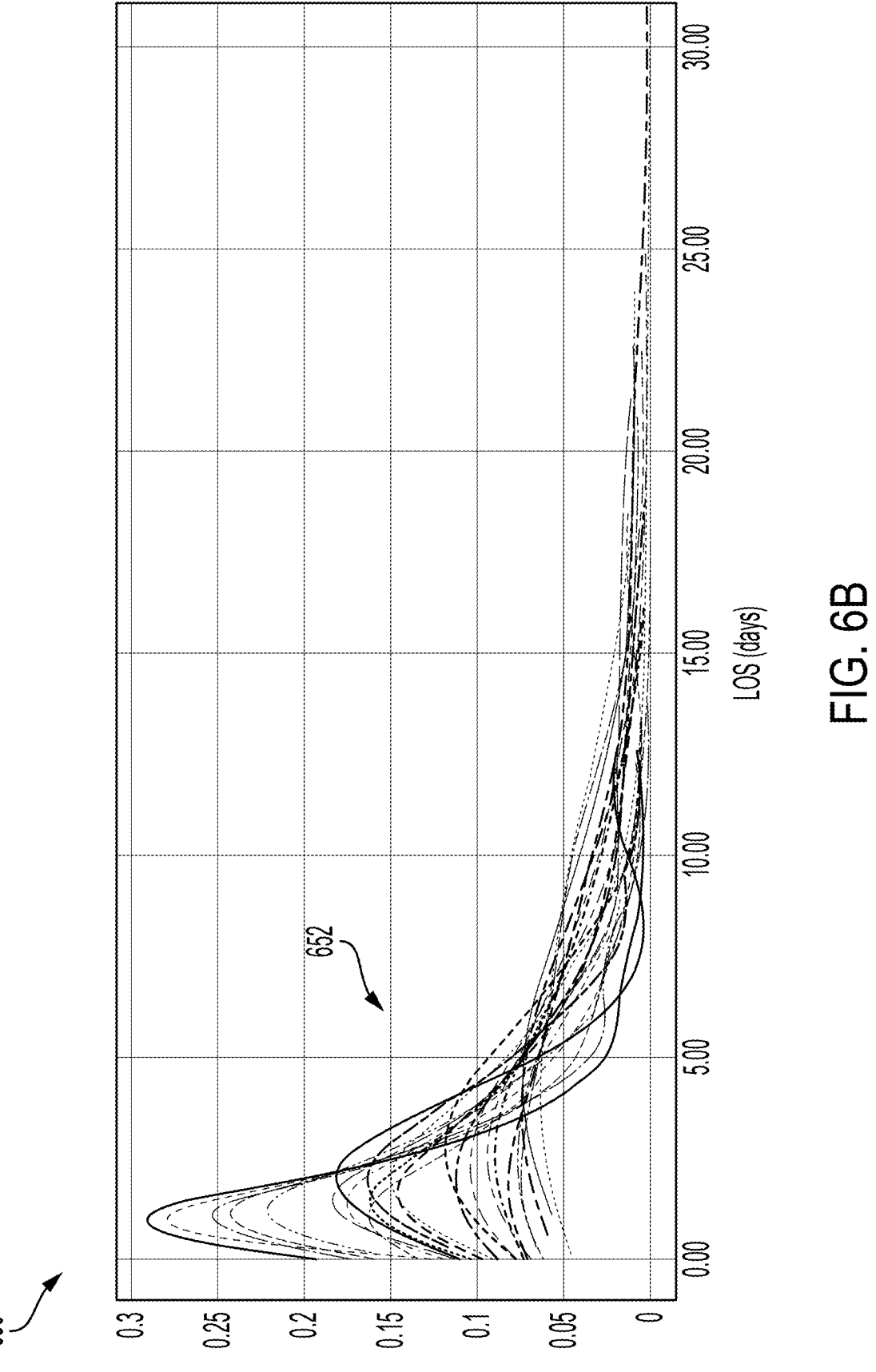
FIG. 6B illustrates a graph of a derived probability density function derived from the observed length-of-stay metrics according to an example.

In various examples, Table 2 may represent the non-standardized patient flow information of Table 1 in a standardized format. For example, the controller 202 may receive the non-standardized patient flow information depicted in Table 1 from either the first hospital or the second hospital and convert the non-standardized patient flow information into standardized patient flow information, as indicated by Table 2. Each row of Table 2 may correspond to a discrete event in the patient's care, and may be defined by one or more standardized parameters indicated in each column of Table 2. For example, the final row of Table 2 indicates that a patient with patient-identification number 34567 and visit-identification number 765432 was discharged on Feb. 4, 2024, at 4:55 PM. The right-hand column of Table 2 indicates various standardized parameters about the discharge, each parameter being separated by the "|" symbol. For example, the standardized parameters indicate the patient was discharged by car to travel to a rehabilitation FIG. 6B illustrates a graph 650 of a derived probability density function derived from the observed length-of-stay metrics (illustrated in FIG. 6A) according to an example. For example, the controller 202 may implement a kernel density function to derive the probability density function for each hospital unit. The graph 650 includes a plurality of traces 652, each corresponding to a probability density function for a respective hospital unit and being derived from the data indicated by a respective row of the rows 602. Each probability density function indicates a probability of a patient having a certain length-of-stay in a corresponding unit. Each probability density function may alternatively be considered a probability of the amount of time that a patient spends in that unit before leaving that unit. For example, a patient may leave the unit either to be transferred to another unit or to be discharged from the hospital from the respective unit.

Although the graph 650 indicates a modeled probability density function for a patient's total length of stay in a respective hospital unit (corresponding to an expected time of discharge), the controller 202 may model other probabilities at act 406. For example, the controller 202 may generate similar probability density functions for various standardized parameters, such as total time waiting for a bed in a cardiology unit, total time spent in a medicine unit, total time between arrival and being admitted, and so forth. Act 406 may therefore include the controller 202 modeling any of a variety of parameters by generating models derived from the standardized information.

At act 408, the controller 202 parameterizes the actual probability distributions determined at act 406. Whereas act 406 includes generating actual probability distributions based on actual observed patient flow information, act 408 includes matching the actual probability distributions to any of various known mathematical models (that is, mathematical functional forms). Parameterizing the actual probability distribution functions may therefore include the controller 202 fitting the actual probability distribution functions to one of various mathematical function distributions, such as a Beta distribution, a normal distribution, a Poisson distribution, a non-homogenous Poisson distribution, an Erlang distribution, a lognormal distribution, a uniform distribution, an exponential distribution, a triangular distribution, a gamma distribution, a Johnson distribution, a Weibull distribution, an empirical discrete distribution, an empirical continuous distribution, or some other distribution. In particular, the controller 202 may select parameters for a closest-fitting distribution to minimize an error between the actual probability distribution and the modeled probability distribution (for example, via a least-squares error-minimization approach).

Figure 7A:
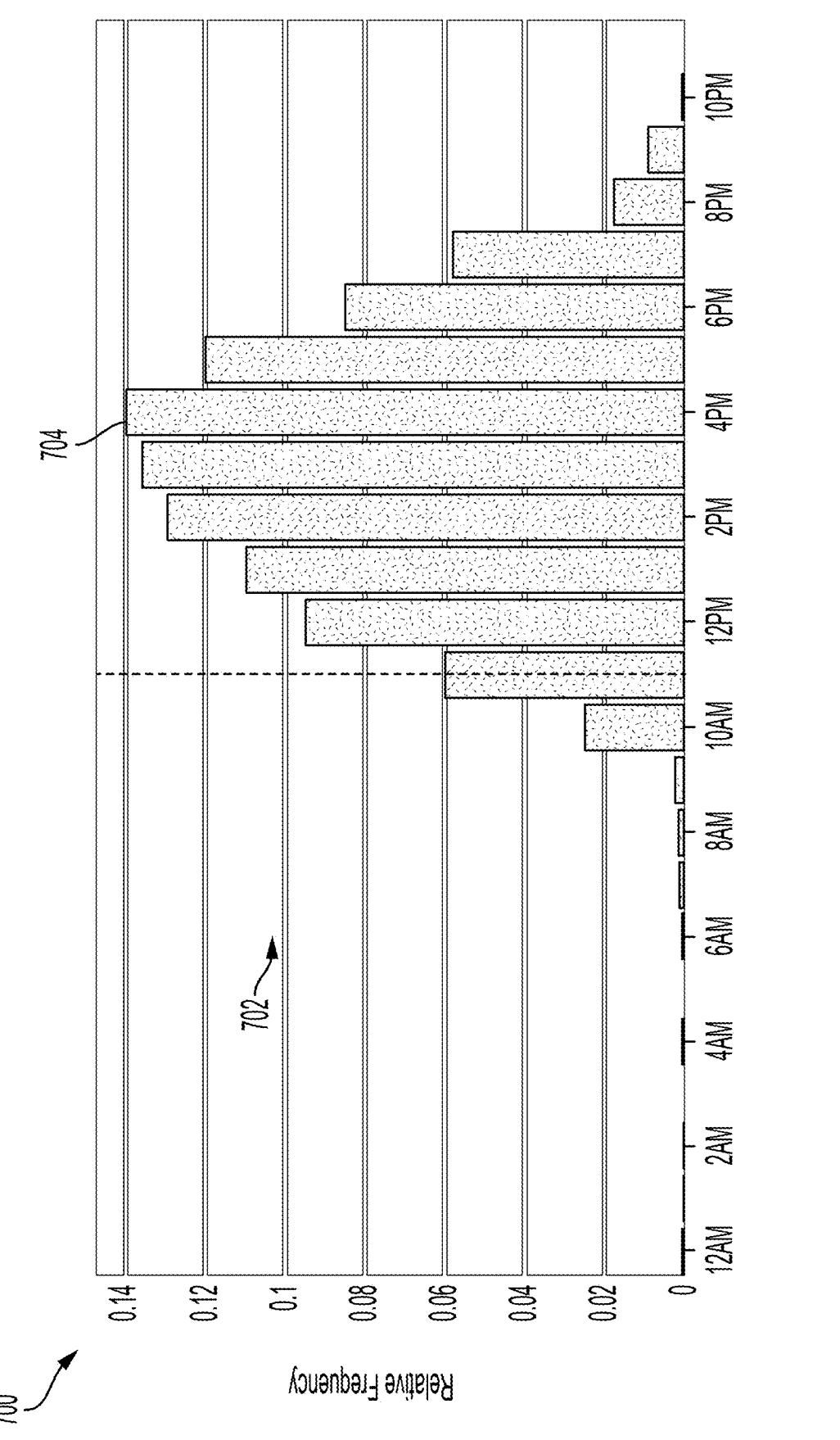
FIG. 7A illustrates a daily optimal discharge histogram for a single day in a given hospital unit according to one example.

At act 410, the controller 202 derives an optimal discharge histogram using the model generated at act 408. FIG. 7A illustrates a daily optimal discharge histogram 700 for a single day in a given hospital unit according to one example. The histogram 700 includes a plurality of data bars 702. A data point is generated for each hour of a day, indicating an hour during which a patient may be discharged. A height of each of the rectangles 702 indicates a relative frequency of a patient being discharged in the corresponding hour of the day. For example, a 5 PM data bar 704 indicates a relative frequency of discharging a patient between 4 PM and 5 PM. As indicated by the 5 PM data bar 704, there is a discharge frequency of approximately 0.1 between 4 PM and 5 PM.

Figure 7B:
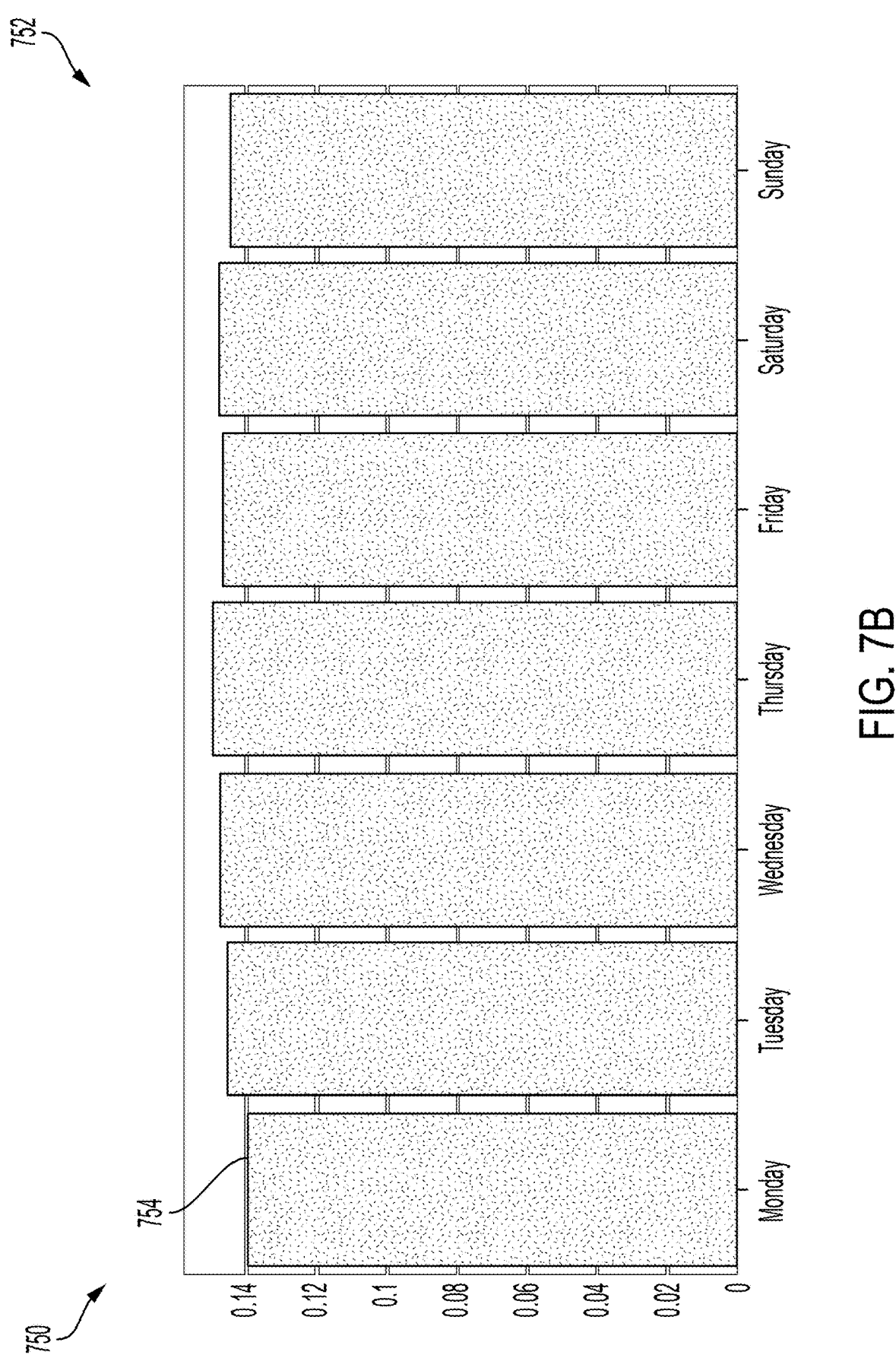
FIG. 7B illustrates a weekly optimal discharge histogram for a single week in a given hospital unit according to one example.

FIG. 7B illustrates a weekly optimal discharge histogram 750 for a single week in a given hospital unit according to one example. The histogram 750 includes a plurality of data bars 752. A data bar is generated for each day of a week, indicating a day on which a patient may be discharged. A height of each of the bars 752 indicates a relative frequency of a patient being discharged in the corresponding day of the week. For example, a Monday data bar 754 indicates a relative frequency of discharging a patient on a Monday. As indicated by the Monday data bar 754, there is a discharge frequency of approximately 0.14 on Monday.

Act 410 may include generating both of the histograms 700, 750. To derive the optimal discharge histogram according to one example, each combination of parameters parameterized at act 408 (for example, hundreds or thousands of different combinations of the parameters) may be experimentally adjusted. These parameters may be similar to those parameterized at act 408. However, whereas the parameters parameterized at act 408 are based on actual historical data for actual patients, the adjusted parameters may represent artificial experimental adjustments. For example, adjusting the parameters may result in decreasing a time that each patient spends waiting for a bed in the cardiology unit by 5%, and determining how that adjustment affects total discharge rates.

For each new adjustment, a new model may be generated in a similar manner as in act 406. For example, a new model may be generated showing an experimental probability density function if the time that each patient spends waiting for a bed in the cardiology unit is decreased by 5%. Thus, whereas the probability density function modeled at act 406 may represent an actual probability of a patient being discharged based on historical data, the new models generated at act 410 may be based on artificial experimental adjustments. These models, which may each include a probability density function for discharge likelihood, may be used to generate a discharge histogram corresponding to the probability density function.

The new models generated at act 410 may be compared to identify at least one optimal discharge histogram. Optimal may be defined as minimizing or maximizing one or more target parameters. For example, an optimal discharge histogram may be one that leads to minimized emergency department boarding times, minimized post-anesthesia care unit boarding times, minimized intensive and/or intermediate care unit transfer times, and minimized overall length-of-stay times. Minimizing these factors may be considered optimal because patient medical outcomes are improved by minimizing these factors. For example, a patient's condition may worsen the longer they are boarded in the emergency department while waiting to receive treatment in a cardiac unit. Indeed, some patients may suffer permanent medical issues that could otherwise have been avoided had they received treatment just an hour earlier. Accordingly, the optimal discharge histograms 700, 750 represent a relative frequency of discharges that, if followed (that is, by discharging patients at the times and frequencies indicated by the histogram 700), will lead to optimizing target parameters and thereby improving medical outcomes of the patients.

In summary, act 410 may include generating hundreds or thousands of models, each model representing the effect of adjusting one or more of dozens or hundreds of parameters on overall length-of-stay, amongst other target parameters. Moreover, this process is performed for every unit in a hospital and is thus performed many times over. This process is performed on a hospital-by-hospital basis; that is, an optimal discharge histogram generated for one hospital may not be applicable to another hospital. Such complex modeling cannot be performed in the human mind, even with pen and paper. Thus, while some hospitals implement a discharge-before-noon paradigm for convenience and ease of implementation, such a paradigm does not yield the optimal discharge histograms 700, 750 generated at act 410. This technical problem—for example, longer patient lengths-of-stay due to suboptimal discharge timing—is solved by the technical solution provided by the process 400, which yields an optimal discharge timetable and thus improved patient-experience metrics (for example, reduced lengths-of-stay).

At act 412, the controller 202 forecasts future discharge numbers for each hospital unit. For example, the controller 202 may forecast an anticipated number of patients that are predicted to be discharged at various points of time in the future. In one example, the controller 202 may forecast the anticipated number of patients that are to be discharged for each week in the next month, or any other length of time. Forecasting the anticipated number of patients that are predicted to be discharged may be determined at least in part based on historical discharge numbers for similar situations (for example, for similar times of year in past years).

Figure 8:
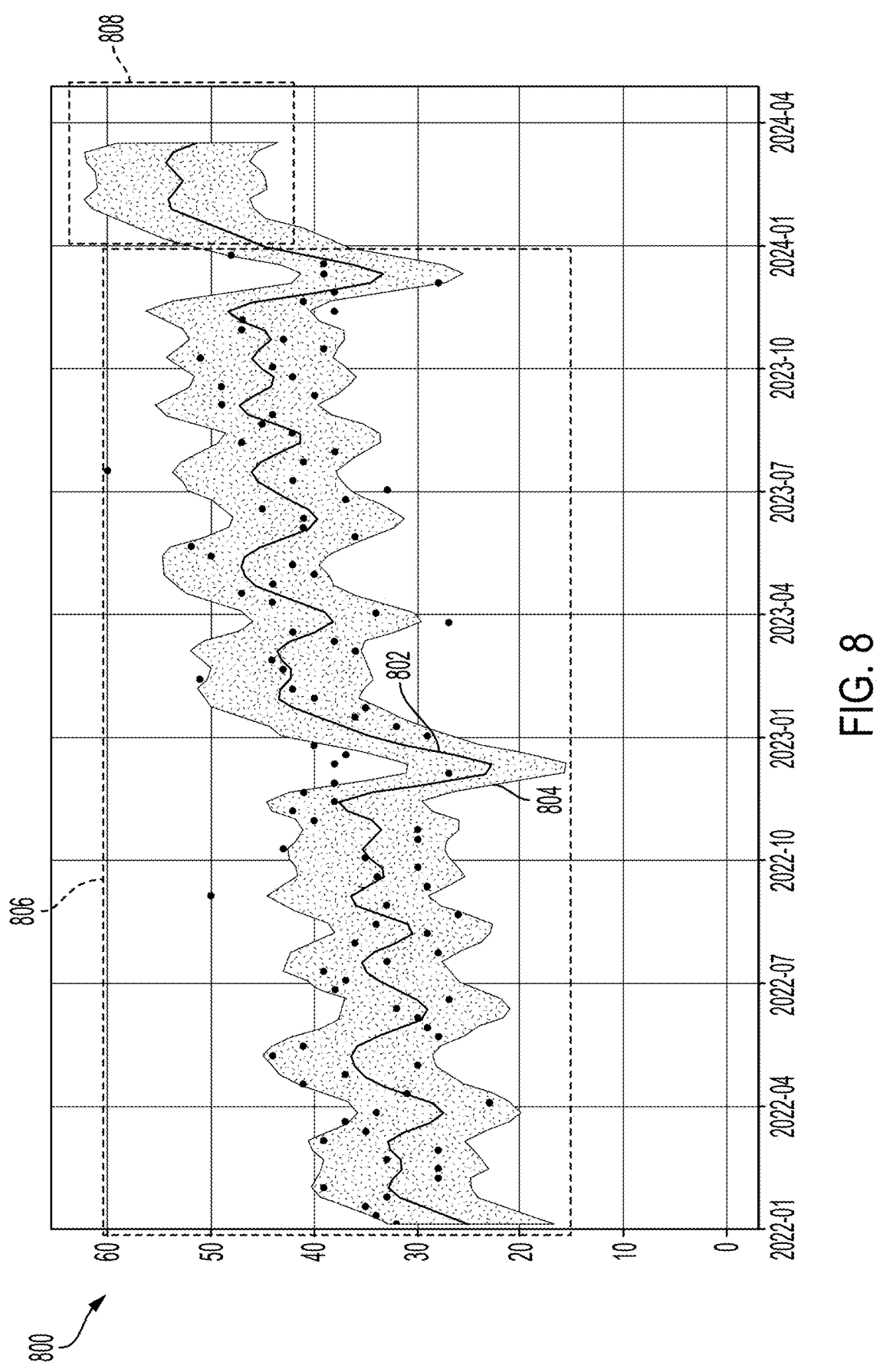
FIG. 8 illustrates a forecast graph indicating a historical and forecasted number of weekly discharges for a given hospital unit according to an example.

FIG. 8 illustrates a forecast graph 800 indicating a historical and forecasted number of weekly discharges for a given hospital unit according to an example. The forecast graph 800 includes a predicted-discharge trace 802 indicating a predicted number of discharges for a given time, and a confidence interval 804 indicating a specific confidence (for example, 80% confidence) around the predicted number of discharges. The predicted-discharge trace 802 and the confidence interval 804 are generated for both a historical period of time 806 for which actual numbers of discharges have already been recorded, and a predicted future period of time 808 which has yet to come to pass. The predicted-discharge trace 802 and the confidence interval 804 are generated using the data points in the historical period of time 806, such data points including, for example, daily or weekly numbers of discharges. The predicted-discharge trace 802 and the confidence interval 804 may then be used to forecast the number of discharges that are forecasted to occur during the predicted future period of time 808.

At act 414, the controller 202 derives at least one optimal patient discharge timetable. Act 414 may include deriving an optimal patient discharge timetable for one or more days over some period of time, such as the next day or the day after, for each hospital unit. The controller 202 derives the at least one optimal patient discharge timetable using at least one optimal discharge histogram (for example, the histograms 700, 750) determined at act 410, and using a forecasted number of discharges (for example, indicated by the forecast graph 800) determined at act 412.

For example, the forecast graph 800 may indicate that a given hospital unit is forecasted to have 27 discharges for a given week. The weekly optimal discharge histogram 750 may be applied to the forecasted number of discharges for the week to determine the optimal number of discharges per day. For example, as discussed above, the Monday data bar 754 indicates that discharges on Monday have a frequency of approximately 0.14. Thus, for a week in which 27 patients are discharged, it may be optimal to discharge 14% of the 27 patients on Monday, or approximately four patients. The weekly optimal discharge histogram 750 may be applied for each day of the week to determine how many of the 27 patients to discharge each day. A similar process may then be executed by applying, for example, the daily optimal discharge histogram 700 to the four patients on the given Monday to determine which time slot (for example, which hour of the day) the patient should be discharged in.

Act 414 may therefore include the controller 202 deriving at least one optimal patient discharge timetable that minimizes a difference between the actual discharges to date for a given day of the week (which may be derived at act 406), and an optimal discharge time for patients on that given day of the week (which may be derived at act 410). Expressed mathematically, this process may be defined by Equation (1) as, $$\min \sum_i (z_i - T_i)^2$$

where min is a minimization function, i is an index of an hour of a day, $T_i$ is a target discharge rate at hour i. $z_i$ is current discharge rate defined in the constraints as follows, $$\text{s.t. } z_i = \frac{x_i + b_i}{D + \sum_i b_i}$$

where $b_i$ is the up to date number of discharges at hour i, D is the total number of discharges for a given day, variable $x_i$ is the number of discharges at hour i, and satisfies $$\sum_j d_{ij} = x_i$$

for each hour i where j is an index of discharges and $$\sum_i d_{ij} = 1$$

where $d_{ij}$ is a binary variable, which equals to one if discharge j is assigned to hour i.

As noted above, FIGS. 3A and 3B illustrate examples of optimal discharge timetables 300, 350 which may be generated as a result of act 414.

At act 416, the controller 202 provides the at least one optimal patient discharge timetable to medical personnel. For example, the controller 202 may control the user interface 204 to display a visual depiction of the at least one optimal patient discharge timetable to medical personnel. Using the daily optimal discharge timetable 300 as an example, medical personnel working in the "1W" hospital unit can easily determine at a glance that one patient should be discharged between 1 PM and 2 PM, and one patient should be discharged between 4 PM and 5 PM.

Accordingly, the controller 202 may execute the process 400 to provide, via a graphical user interface (for example, the display device 212), an optimal discharge timetable for some period of time, such as for the next week. In some examples, a new optimal discharge timetable may be generated at some regular interval, such as each day. For example, consider an example in which optimal discharge timetables (for example, similar to the optimal discharge timetable 300) are generated for each day of the next week, from January $1^{st}$ to January $8^{th}$. On January $2^{nd}$, the optimal discharge timetable for January $1^{st}$ may no longer be displayed (for example, because January $1^{st}$ has passed), but a new optimal discharge timetable for January $9^{th}$ may be generated (for example, because January $9^{th}$ is now a week away).

In generating the new optimal discharge timetable for January $9^{th}$, the controller 202 may attempt to minimize a difference between actual historical discharges and an optimal cumulative unit and hospital-specific discharge pattern. For example, if January $9^{th}$ is a Tuesday, the controller 202 may generate each unit's January $9^{th}$ optimal discharge timetable by considering actual discharge data from all previous Tuesdays, and attempting to minimize the difference between the actual discharges on all previous Tuesdays and the desired optimal probability discharge function of discharges for January $9^{th}$.

When a new optimal discharge timetable for January $9^{th}$ is generated, the previously determined optimal discharge timetables for January $2^{nd}$ through January $8^{th}$ may not be altered. That is, once an optimal discharge timetable is generated for a particular day, the optimal discharge timetable may not be updated even if new information is subsequently acquired. Once an optimal discharge timetable is generated, it may be accessible for the next week (or some other period of time), but the optimal discharge timetable may not be updated or replaced, even if new information becomes available.

In other examples, the controller 202 may update previously determined optimal discharge timetables. The controller 202 may update at least one optimal discharge timetable if, for example, medical personnel are deviating from the timetable. Medical personnel may use the user interface 204 (which may include, for example, a mouse and keyboard) to input information indicative of when a patient has been discharged. For example, part of the discharge process may include the medical personnel inputting a time of discharge via the user interface 204, thus creating a record each time a patient is discharged. The controller 202 may use this discharge data to record an indication of the discharge, and store the indication of the discharge in the memory 206. The controller 202 may update at least one optimal discharge timetable based on this discharge data in real-time, and/or at a regular frequency, such as every day.

For example, a real-time update may include updating an optimal discharge timetable based on real-time deviations between actual discharges on a given day and an optimal discharge timetable for the given day. Suppose that an optimal discharge table indicates that medical personnel should discharge a patient by 2 PM, but the medical personnel are unable to do so. In that case, the controller 202 may determine that the at least one optimal discharge timetable should be updated to generate a new timetable that takes into account the fact that a patient was not discharged by 2 PM. For example, a new optimal timetable may be generated indicating that a patient should be discharged by 3 PM now that a patient cannot be discharged by 2 PM. This process may occur in real-time, that is, as soon as 2 PM passes (and no patient has been discharged).

A regular update may include updating an optimal discharge timetable at certain regular intervals, such as at a certain time every day. For example, optimal discharge timetables may be updated, or a determination may be made as to whether to update the timetables, at midnight of each day. Continuing with the example above, an optimal discharge timetable may be generated for January $9^{th}$ once January $1^{st}$ passes. As discussed above, in some examples, the optimal discharge timetables previously generated for January $2^{nd}$ through January $8^{th}$ may not be updated with each passing day. In various examples, however, the optimal discharge timetables previously generated for January $2^{nd}$ through January $8^{th}$ may be updated if, for example, new pertinent information is available that was not available when the optimal discharge timetables were originally generated. Such new information may include discharge data indicating that medical personnel were unable to discharge enough patients on January $1^{st}$, thereby impacting later discharges on January $2^{nd}$ through January $8^{th}$.

In various examples, updating an optimal discharge timetable may simply include updating the timetable to display an indication that the medical personnel are not complying with the discharge timetable. Such an indication might include, for example, a clock indicating how long overdue the discharge is, a counter indicating how many patient discharges behind schedule the medical personnel are, and so forth. In some examples, updating may include automatically generating a message containing updated information about the deviation from the timetable, which is displayed as part of, or in conjunction with, the updated timetable.

That is, in some examples, the content of the timetable itself may not be updated except that a message is generated and displayed along with the timetable indicating deviations from the timetable. This message may be transmitted to multiple users in a hospital unit, or even multiple users in a hospital outside of the hospital unit. For example, if all medical personnel who manage patient discharge have computing devices similar to or implementing the discharge-optimization system 200, each corresponding user interface 204 may receive and display the message such that each user has immediate access to up-to-date patient information. Thus, updating the optimal discharge timetable may include automatically generating a message containing updated information about deviations from the timetable whenever updated information (for example, deviation information) is acquired, and transmitting the message to multiple users (for example, over a computer network, such as via the network interface 208) in real-time as deviations occur, so that each user has immediate access to up-to-date patient information.

In various examples, the controller 202 updates the discharge timetable in real-time. For example, the controller 202 may monitor a current time of day and, if the time passes a deadline by which a patient is to be discharged, the controller 202 may immediately evaluate whether a patient has been discharged. The controller 202 may then update the timetable as necessary. For example, if a patient is to be discharged by 2 PM, the controller 202 may evaluate whether a patient has been discharged in real-time as the clock indicates a time of 2 PM, and then update the timetable in real-time (for example, on the order of a few milliseconds or second) to reflect the medical personnel's adherence or divergence from the timetable.

Accordingly, the controller 202 may execute the process 400 to provide, via a graphical user interface, an optimal discharge timetable. As medical personnel discharge patients, the medical personnel may input indications of which patients have been discharged and when. For example, the medical personnel may input these indications via the user interface 204, which may include the same graphical user interface on which the timetable is displayed.

In some examples, the controller 202 may automatically update the graphical user interface, in real-time in some examples, based on these inputs. Accordingly, the process of updating the graphical user interface is a practical application. Specifically, the controller 202 executes a specific manner of automatically displaying and updating timetables to the user based on medical-personnel inputs. In other examples, the controller 202 may not update previously generated optimal discharge timetables, but may account for any deviations between actual discharges and optimal discharges when generating new optimal discharge timetables.

These examples provide a specific improvement of prior systems, such as systems that do not provide discharge timetable objectives. Because these systems fail to provide discharge targets, medical personnel do not have the information necessary to know if actual discharges are keeping pace with an optimal discharge schedule, because no optimal discharge schedule has been identified. The controller 202 thus provides an interface that results in an improved user interface for electronic devices, because medical personnel can more quickly and easily understand how effectively patients are being discharged. This improved graphical user interface, which displays (and, in some examples, automatically updates) discharge targets and/or deviations therefrom in real-time to identify discrepancies between a target and actual discharge rates, therefore provides a practical application of a technical solution to this technical problem.

In some examples, a hospital may include several computing devices including or implementing the discharge-optimization system 200. These computing devices may be communicatively coupled to one another via a communication network. For example, from the perspective of a given discharge-optimization system 200, the external devices 210 may include one or more other discharge-optimization systems. In various examples, each of these multiple discharge-optimization systems 200 may update their respective user interfaces 204 in real-time. For example, if a discharge target is missed in a given hospital unit, every user interface 204 of every networked discharge-optimization system 200 may update in real-time to reflect the missed target.

Generating optimal discharge timetables therefore provides a technological solution (for example, generating an optimized discharge timetable which may be updated automatically based on adherence to or divergence from discharge targets, such as by generating alerts indicative of the deviation) to a technological problem (for example, optimizing patient discharges). Generating and implementing discharge timetables as discussed herein dramatically improves patient experience in a hospital, such as by reducing patient boarding and transfer times. Furthermore, patient care may be improved because patients may be cared for in an appropriate setting (for example, in an appropriate inpatient hospital unit rather than, for example, the emergency department where they may be temporarily boarded).

For example, FIG. 9A illustrates a boarding-time table 900 indicating boarding times in various units within a hospital. A first column 902 indicates a unit in the hospital, identified as Unit A, Unit B, Unit C, and so forth. Each of the units may correspond to a unit in a hospital such as an organ transplant unit, a neurology intermediate care unit, an acute medicine unit, and so forth. A second column 904 indicates a baseline boarding time for each unit. A baseline boarding time may include boarding times (that is, a time spent in a respective hospital unit) before optimal discharge timetables are generated and implemented by medical personnel. A third column 906 indicates boarding times for each unit if optimal discharge timetables are implemented.

As indicated by the third column 906 compared to the second column 904, implementing optimal discharge timetables substantially reduces boarding times in nearly every unit. For example, average emergency department boarding times corresponding to patients who are subsequently admitted to Unit A are reduced from 15.8 hours to 11.7 hours, a 25.6% improvement. Average emergency department boarding times for patients who are subsequently admitted to Unit B are reduced from 14.1 hours to 9.4 hours, a 33.3% improvement. Average emergency department boarding times for patients who are subsequently admitted to Unit C are reduced from 13.3 to 10.0 hours, a 24.8% improvement. Accordingly, the technical solution provided by the optimal discharge timetables yields substantial and demonstrative improvements to the technical problem of improving patient care by reducing emergency department boarding times.

Figure 9B:
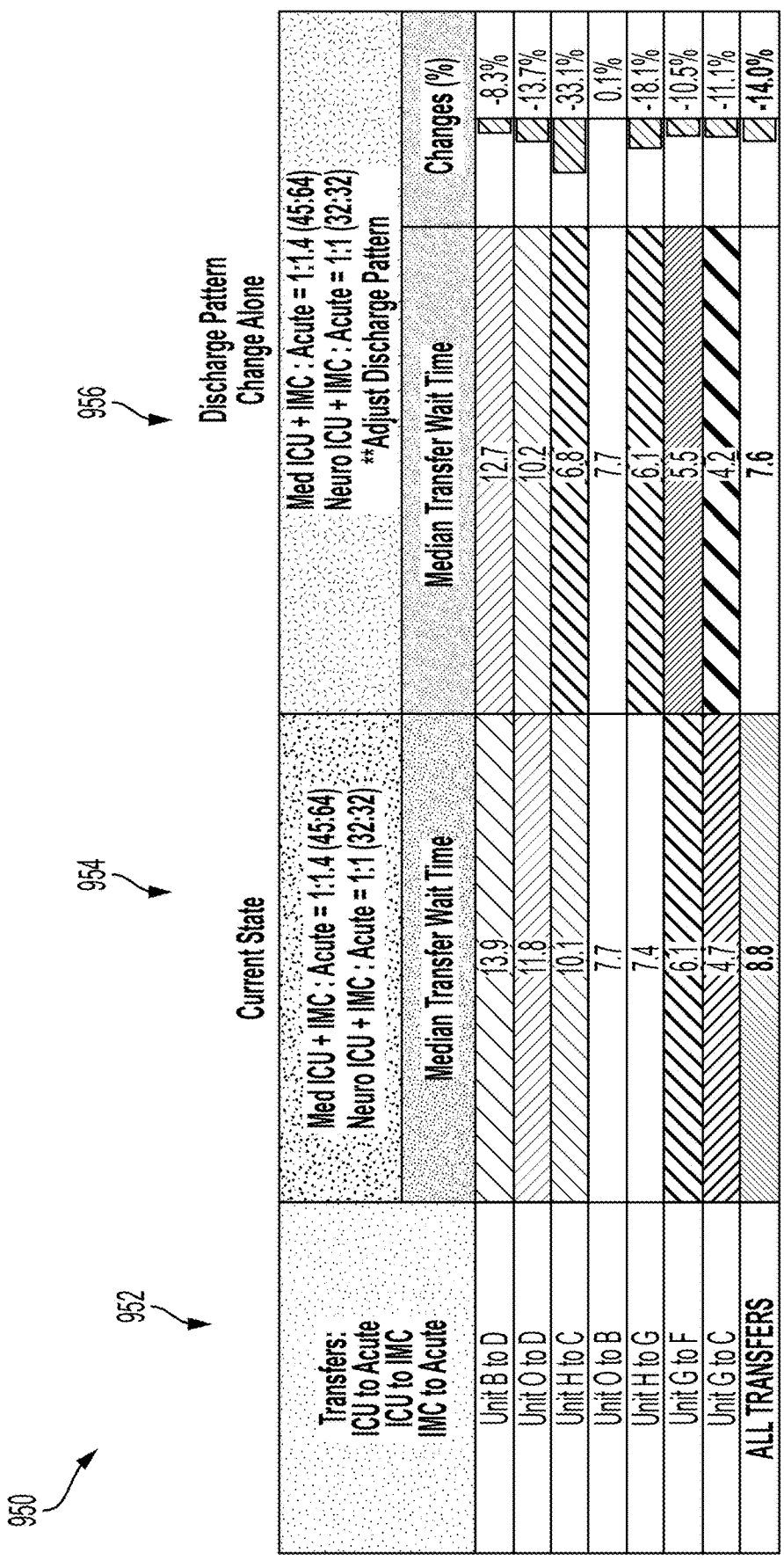
FIG. 9B illustrates a transfer-waiting-time table indicating transfer-waiting times between various units within a hospital.

FIG. 9B illustrates a transfer-waiting-time table 950 indicating transfer-waiting times (that is, the time that a patient spends waiting to be transferred after a decision has been made to execute the transfer) between various units within a hospital. A first column 952 indicates units between which patients are transferred in a hospital, such as from Unit B to Unit D, from Unit O to Unit D, from Unit H to Unit C, and so forth. A second column 954 indicates a baseline transfer-waiting time for each unit. A baseline transfer-waiting time may include the time that a patient spends waiting to be transferred after a decision has been made to execute the transfer before optimal discharge timetables are generated and implemented by medical personnel. A third column 956 indicates transfer-waiting times for each unit if optimal discharge timetables are implemented.

As indicated by the third column 956 compared to the second column 954, implementing optimal discharge timetables substantially reduces transfer-waiting times in nearly every unit. For example, the average waiting time to transfer from Unit B to Unit D is reduced from 13.9 to 12.7 hours, an 8.3% improvement. The average waiting time to transfer from Unit O to Unit D is reduced from 11.8 to 10.2 hours, a 13.7% improvement. The average waiting time to transfer from Unit H to Unit C is reduced from 10.1 to 6.8 hours, a 33.1% improvement Accordingly, the technical solution provided by the optimal discharge timetables yields substantial and demonstrative improvements to the technical problem of improving patient care by reducing transfer-waiting times.

As noted above, the discharge-optimization system 200 includes a controller 202, a user interface 204, memory 206, and a network interface 208, which may be coupled to the external devices 210.

The controller 202 may execute various operations discussed above. The controller 202 may also execute one or more instructions stored on one or more non-transitory computer-readable media. For example, the memory 206 and/or the external devices 210 may include or be coupled to the non-transitory computer-readable media which store instructions 214. The controller 202 may execute the instructions 214 to execute various operations discussed above, including the process 400. In some examples, the controller 202 may include one or more processors or other types of controllers. In one example, the controller 202 is or includes at least one processor. In another example, the controller 202 performs at least a portion of the operations discussed above using an application-specific integrated circuit tailored to perform particular operations in addition to, or in lieu of, a processor. As illustrated by these examples, examples in accordance with the present disclosure may perform the operations described herein using many specific combinations of hardware and software and the disclosure is not limited to any particular combination of hardware and software components. Examples of the disclosure may include a computer-program product configured to execute methods, processes, and/or operations discussed above. The computer-program product may be, or include, one or more controllers and/or processors configured to execute instructions to perform methods, processes, and/or operations discussed above.

The user interface 204 may include one or more user inputs, one or more user outputs, or a combination thereof. The user interface 204 may include user-input devices such as a keyboard, a mouse, a touchscreen, and so forth. Users, such as medical personnel, may use the user inputs to input information indicative of a patient's current status in the hospital and/or a current status of patient discharges in the hospital. The user interface 204 may also include user-output devices such as a computer monitor, sound-emitting devices such as speakers or buzzers, light-emitting devices such as light-emitting diodes, and so forth. Users, such as medical personnel, may use the user outputs to receive information indicative of optimal discharge timetables and whether and to what degree the current discharge performance deviates from the optimal discharge timetables.

The memory 206 may include non-transitory computer-readable media, such as memory devices (for example, read-only memory, random-access memory, and so forth) and/or storage devices (for example, hard drives, optical disks, and so forth).

The network interface 208 may include one or more devices or components to interface with external devices, such as the external devices 210. For example, the network interface 208 may include wired-communication components that enable wired communication (for example, wired-communication ports to receive a communication wire), wireless-communication components that enable wireless communication (for example, antennas), a combination thereof, and so forth.

The external devices 210 may include any devices or components which are physically external to the discharge-optimization system 200, such as external computing devices (for example, other computing devices within a hospital), cloud computers, servers, external data storage, and so forth. In some examples, the external devices 210 may include devices substantially similar to the discharge-optimization system 200. For example, a hospital may include several computing devices implemented as or including the discharge-optimization system 200, each of which may be networked together. In one example, each hospital unit may include a dedicated team of discharge professionals who manage patient discharges, and each of these teams (or even each member of each team) may have one or more computing devices substantially similar to the discharge-optimization system 200.

Having thus described several aspects of at least one embodiment, it is to be appreciated various alterations, modifications, and improvements will readily occur to those skilled in the art. Such alterations, modifications, and improvements are intended to be part of, and within the spirit and scope of, this disclosure. Accordingly, the foregoing description and drawings are by way of example only.

What is claimed is:

1. A method of operating a patient-discharge-optimization system to improve medical outcomes, the method comprising:

accessing, from memory and/or storage, historical patient flow information including a plurality of timestamped events for each patient of a plurality of patients;

converting, by the discharge-optimization system, the historical patient flow information into standardized flow information having a standardized format defined by a plurality of standardized parameters;

generating, by the discharge-optimization system, a plurality of models, each model indicating an effect of modifying at least one parameter of the plurality of standardized parameters for each patient of the plurality of patients;

deriving, by the discharge-optimization system and based on the plurality of models, an optimal discharge histogram for one or more days;

forecasting, based on the historical patient flow information, an anticipated future number of discharges for the one or more days;

deriving an optimal patient discharge timetable for the one or more days based on the optimal discharge histogram and the anticipated future number of discharges, the optimal patient discharge timetable being indicative of an optimal number of patients to discharge on each of the one or more days;

transmitting the optimal patient discharge timetable over a computer network to one or more users in real-time;

receiving deviation information indicative of a deviation from the optimal patient discharge timetable;

automatically updating the optimal patient discharge timetable based on the deviation from the optimal patient discharge timetable responsive to receiving the deviation information; and transmitting a message indicative of updating the optimal patient discharge timetable to the one or more users over the computer network in real-time so that each user of the one or more users has immediate access to up-to-date patient information.

2. The method of claim 1, wherein the historical patient flow information is stored in the memory and/or storage in a non-standardized format.

3. The method of claim 2, further comprising storing, by the discharge-optimization system after converting the non-standardized historical patient flow information into the standardized flow information, the standardized flow information in the standardized format in the memory and/or storage.

4. The method of claim 1, wherein deriving the optimal patient discharge timetable includes determining, for each day of the one or more days, a number of patients to be discharged on each day and a respective window of time for each patient during which to discharge the respective patient.

5. The method of claim 1, wherein the optimal discharge histogram indicates an optimal relative frequency to discharge patients for each window of time of a plurality of windows of time within a day.

6. The method of claim 1, wherein deriving the optimal patient discharge timetable for the one or more days includes deriving, for each hospital unit in a hospital including a plurality of units, a respective optimal patient discharge timetable for each day of the next week.

7. At least one non-transitory computer-readable medium storing thereon sequences of computer-executable instructions for operating a discharge-optimization system, the sequences of computer-executable instructions including instructions that instruct at least one processor to:

access historical patient flow information including a plurality of timestamped events for each patient of a plurality of patients;

convert the historical patient flow information into standardized flow information having a standardized format defined by a plurality of standardized parameters;

generate a plurality of models, each model indicating an effect of modifying at least one parameter of the plurality of standardized parameters for each patient of the plurality of patients;

derive, based on the plurality of models, an optimal discharge histogram for one or more days;

forecast, based on the historical patient flow information, an anticipated future number of discharges for the one or more days;

derive an optimal patient discharge timetable for the one or more days based on the optimal discharge histogram and the anticipated future number of discharges, the optimal patient discharge timetable being indicative of an optimal number of patients to discharge on each of the one or more days;

transmit the optimal patient discharge timetable over a computer network to one or more users in real-time;

receive deviation information indicative of a deviation from the optimal patient discharge timetable;

automatically update the optimal patient discharge timetable based on the deviation from the optimal patient discharge timetable responsive to receiving the deviation information; and transmit a message indicative of updating the optimal patient discharge timetable to the one or more users over the computer network in real-time so that each user of the one or more users has immediate access to up-to-date patient information.

8. The at least one non-transitory computer-readable medium of claim 7, wherein the historical patient flow information is stored in a non-standardized format.

9. The at least one non-transitory computer-readable medium of claim 8, wherein the instructions further instruct the at least one processor to store, after converting the non-standardized historical patient flow information into the standardized flow information, the standardized flow information in the standardized format in memory and/or storage.

10. The at least one non-transitory computer-readable medium of claim 7, wherein deriving the optimal patient discharge timetable includes determining, for each day of the one or more days, a number of patients to be discharged on each day and a respective window of time for each patient during which to discharge the respective patient.

11. The at least one non-transitory computer-readable medium of claim 7, wherein the optimal discharge histogram indicates an optimal relative frequency to discharge patients for each window of time of a plurality of windows of time within a day.

12. The at least one non-transitory computer-readable medium of claim 7, wherein deriving the optimal patient discharge timetable for the one or more days includes deriving, for each hospital unit in a hospital including a plurality of units, a respective optimal patient discharge timetable for each day of the next week.

13. A discharge-optimization system comprising:
at least one graphical user interface; and
at least one controller configured to:
    access historical patient flow information including a plurality of timestamped events for each patient of a plurality of patients;
    convert the historical patient flow information into standardized flow information having a standardized format defined by a plurality of standardized parameters;
    generate a plurality of models, each model indicating an effect of modifying at least one parameter of the plurality of standardized parameters for each patient of the plurality of patients;

derive, based on the plurality of models, an optimal discharge histogram for one or more days;
forecast, based on the historical patient flow information, an anticipated future number of discharges for the one or more days;
derive an optimal patient discharge timetable for the one or more days based on the optimal discharge histogram and the anticipated future number of discharges, the optimal patient discharge timetable being indicative of an optimal number of patients to discharge on each of the one or more days;
control the at least one graphical user interface to display the optimal patient discharge timetable to one or more users;
receive deviation information indicative of a deviation from the optimal patient discharge timetable;
automatically updating, in real-time, the graphical user interface based on the deviation from the optimal patient discharge timetable; and
transmitting a message indicative of updating the graphical user interface to the one or more users over a computer network in real-time so that each user of the one or more users has immediate access to up-to-date patient information.

14. The system of claim 13, wherein the historical patient flow information is stored in a non-standardized format.

15. The method of claim 1, wherein the deviation information includes time information indicative of a current time.

16. The method of claim 1, wherein the deviation information includes discharge information indicative of a number of discharges.

17. The at least one non-transitory computer-readable medium of claim 7, wherein the deviation information includes time information indicative of a current time.

18. The at least one non-transitory computer-readable medium of claim 7, wherein the deviation information includes discharge information indicative of a number of discharges.

19. The discharge-optimization system of claim 13, wherein the deviation information includes time information indicative of a current time.

20. The discharge-optimization system of claim 13, wherein the deviation information includes discharge information indicative of a number of discharges.

\*    \*    \*    \*    \*